(12) United States Patent
Olivo et al.

(10) Patent No.: US 7,553,646 B2
(45) Date of Patent: Jun. 30, 2009

(54) MICROBIAL SULFOXIDATION AND AMIDATION OF BENZHDRYLSULFANYL CARBOXYLIC ACIDS AND USES THEREOF

(75) Inventors: Horacio F. Olivo, Iowa City, IA (US); Antonio Victor Osorio-Lozada, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 385 days.

(21) Appl. No.: 11/460,532

(22) Filed: Jul. 27, 2006

(65) Prior Publication Data

US 2007/0026507 A1 Feb. 1, 2007

Related U.S. Application Data

(60) Provisional application No. 60/703,322, filed on Jul. 28, 2005.

(51) Int. Cl.
*C12P 13/02* (2006.01)
*A61K 31/16* (2006.01)
*A61K 31/165* (2006.01)
*A01N 37/36* (2006.01)

(52) U.S. Cl. ............. 435/129; 514/618; 514/630; 564/154; 564/162

(58) Field of Classification Search ............... None
See application file for complete search history.

(56) References Cited

U.S. PATENT DOCUMENTS 6,348,500 B1 2/2002 Fu 6,875,893 B2 4/2005 Largeau et al.
2005/0080256 A1* 4/2005 Rebiere et al. .............. 540/607

OTHER PUBLICATIONS

PCT/US2006/029098 International Search Report mailed Mar. 15, 2007.
In, Yasuko et al., "Crystal and Molecular Structure of an (S)-(+)-Enantiomer of Modafinil, a Novel Wake-Promoting Agent", Chem. Pharm. Bull. 52(10):1186-1189 (2004).
Osorio-Lozada et al., "Synthesis and determination of the absolute stereochemistry of the enantiomers of adrafinil and modafinil", Tetrahedron: Asymmetry, 15:3811-3815 (2004).
Prisinzano, Thomas et al., "Synthesis and determination of the absolute configuration of the enantiomers of modafinil", Tetrahedron: Asymmetry, 15:1053-1058 (2004).
Grogan, Gideon et al. "The biocatalytic reactions of Beauveria spp.", J. of Molecular Catalysis B: Enzymatic 9:1-32 (2000).

* cited by examiner

*Primary Examiner*—Herbert J. Lilling
(74) *Attorney, Agent, or Firm*—McKee, Voorhees & Sease, P.L.C.

(57) ABSTRACT

The present invention provides novel methods for the synthesis of racemic and enantiomers of modafinil via microbial oxidation-amidation transformation. The methods include the successive oxidation-amidation of benzhydrylsulfanyl carboxylic acid to produce racemic and enantiomers of modafinil using at least one microorganism of yeast, bacteria, or fungus. Also disclosed are pharmaceutical compositions of racemic and enantiomers of modafinil along with their use in the treatment of diseases, including attention deficit hyperactivity disorder and drug addiction.

18 Claims, No Drawings

MICROBIAL SULFOXIDATION AND AMIDATION OF BENZHDRYLSULFANYL CARBOXYLIC ACIDS AND USES THEREOF

CROSS-REFERENCE TO RELATED APPLICATIONS

This application claims priority under 35 U.S.C. § 119 of provisional application Ser. No. 60/703,322 filed Jul. 28, 2005, which application is hereby incorporated by reference in its entirety.

GRANT REFERENCE

This invention was partially funded by the National Science Foundation, No. EEC-0310689. The government may have certain rights in the invention.

FIELD OF THE INVENTION

The present invention provides processes for the preparation of racemic modafinil, (+)(S)-modafinil and (−)-(R)-modafinil which includes the step of subjecting benzhydrylsulfanyl carboxylic acid to an oxidation-amidation reaction using at least one microorganism.

BACKGROUND OF THE INVENTION

Modafinil is a psychostimulant agent that has garnered attention because of its recent approval by FDA for the treatment of excessive daytime sleepiness and because of its lack of abuse liability. (Divide and Conquer. *Chem. Eng. News* 2004, 82(41), 20, Myrick, H.; Malcolm, R.; Taylor, B.; LaRowe, S. *Ann. Clinic. Psychiatry* 2004, 16, 101-119.) Recent work suggests that modafinil might also be of utility as a treatment of attention deficit/hyperactivity disorder (ADHD), and in treating opioid-induced sedation. (Webster, L; Andrews, M.; Stoddard, G. *Pain Med.* 2003, 4(2), 135-40. (b) Turner D. C.; Clark, L.; Dowson, J.; Robbins, T. W.; Sahakian, B. J. *Biol. Psychiatry* 2004, 55(10), 1031-40.) Although modafinil has a chiral center at the sulfur atom, the racemic sulfoxide is marketed as PROVIGIL modafinil. (world wide web at provigil.com). The exact mechanism of action of modafinil is still unknown. Efforts are directed towards finding their mechanism of action and the physiological differences of its enantiomers.

These efforts have been hindered by current processes to make modafinil, in particular, their inability to synthesize a selective enantiomer of modafinil, lengthy multiple step processes, low yields and the production of environmentally unfriendly waste. For these and other reasons there is a need for the present invention.

BRIEF SUMMARY OF THE INVENTION

A method of producing modafinil using at least one microorganism has now been developed which provides racemic modafinil, (+)-modafinil, and (−)-modafinil via microbial oxidation-amidation transformation. Also disclosed are pharmaceutical compositions of racemic and enantiomeric (+) and (−)-modafinil along with their use in the treatment of diseases.

In one embodiment, the methods of the present invention includes a method of preparing a racemic mixture of modafinil by subjecting benzhydrylsulfanyl carboxylic acid to an oxidation-amidation reaction using at least one microorganism to obtain a sulfoxide-amide product of racemic modafinil.

In another embodiment, racemic modafinil is obtained from the method of subjecting benzhydrylsulfanyl carboxylic acid to an oxidation-amidation reaction using at least one microorganism to obtain a sulfoxide-amide product of racemic modafinil.

In another embodiment, the invention provides a method of preparing a racemic mixture of modafinil by subjecting benzhydrylsulfanyl carboxylic acid to an oxidation-amidation reaction using *Amycolaptosis orientalis* to obtain racemic modafinil.

In yet another embodiment, racemic modafinil is obtained from the method of subjecting benzhydrylsulfanyl carboxylic acid to an oxidation-amidation reaction using *Amycolaptosis orientalis* to obtain racemic modafinil.

In still another embodiment, a method of preparing an (S)-enantiomer of modafinil comprising subjecting benzhydrylsulfanyl carboxylic acid to an oxidation reaction using a microorganism to obtain an (S)-sulfoxide product of (S)-benzhydrylsulfinyl carboxylic acid; and subjecting the (S)-sulfoxide product to an amidation reaction using a microorganism to obtain an (S)-sulfoxide-amide product of (+)-(S)-modafinil is disclosed.

In another embodiment, (+)-(S)-modafinil is obtained from the method of subjecting benzhydrylsulfanyl carboxylic acid to an oxidation reaction using a microorganism to obtain an (S)-sulfoxide product of (S)-benzhydrylsulfinyl carboxylic acid; and subjecting the (S)-sulfoxide product to an amidation reaction using a microorganism to obtain an (S)-sulfoxide-amide product of (+)-(S)-modafinil.

In another aspect, a method of preparing an (+)-(S)-enantiomer of modafinil is disclosed. The method includes subjecting benzhydrylsulfanyl carboxylic acid to an oxidation reaction using *Beauveria bassiana* to obtain (S)-benzhydrylsulfinyl carboxylic acid and subjecting the (S)-benzhydrylsulfinyl carboxylic acid to an amidation reaction using *Bacillus subtilis* to obtain (+)-(S)-modafinil.

In a further embodiment, (+)-(S)-modafinil is obtained from the method of subjecting benzhydrylsulfanyl carboxylic acid to an oxidation reaction using *Beauveria bassiana* to obtain (S)-benzhydrylsulfinyl carboxylic acid and subjecting the (S)-benzhydrylsulfinyl carboxylic acid to an amidation reaction using *Bacillus subtilis* to obtain (+)-(S)-modafinil.

In another embodiment, a method of preparing (−)-(R)-enantiomer of modafinil includes subjecting benzhydrylsulfanyl carboxylic acid to an oxidation reaction using a microorganism to obtain an (R)-sulfoxide product of (R)-benzhydrylsulfinyl carboxylic acid and subjecting the (R)-sulfoxide product to an amidation reaction using a microorganism to obtain an (R)-sulfoxide-amide product of (−)-(R)-modafinil.

In another aspect, (−)-(R)-modafinil is obtained from the method of subjecting benzhydrylsulfanyl carboxylic acid to an oxidation reaction using a microorganism to obtain an (R)-sulfoxide product of (R)-benzhydrylsulfinyl carboxylic acid and subjecting the (R)-sulfoxide product to an amidation reaction using a microorganism to obtain an (R)-sulfoxide-amide product of (−)-(R)-modafinil.

In another embodiment, the invention provides a method of preparing an (−)-(R)-enantiomer of modafinil including subjecting benzhydrylsulfanyl carboxylic acid to an oxidation reaction using *Sphingomonas* sp to obtain (R)-benzhydrylsulfinyl carboxylic acid; and subjecting the (R)-benzhydrylsulfinyl carboxylic acid to an amidation reaction using a bacteria genetically engineered comprising toluene dioxygenase to obtain (−)-(R)-modafinil.

In still another embodiment, (−)-(R)-modafinil is obtained from the method of subjecting benzhydrylsulfanyl carboxylic acid to an oxidation reaction using *Sphingomonas* sp to obtain (R)-benzhydrylsulfinyl carboxylic acid and subjecting the (R) benzhydrylsulfinyl carboxylic acid to an amidation reaction using the bacteria genetically engineered comprising toluene dioxygenase to obtain (−)-(R)-modafinil.

In still another embodiment, a pharmaceutical composition comprising racemic modafinil wherein said modafinil has been obtained by the method comprising subjecting benzhydrylsulfanyl carboxylic acid to an oxidation-amidation reaction using at least one microorganism to obtain a sulfoxide-amide product and a pharmaceutically acceptable carrier or excipient is provided.

In still another embodiment, a pharmaceutical composition comprising (+)-(S)-modafinil, wherein said (+)-(S)-modafinil has been obtained by the method comprising subjecting benzhydrylsulfanyl carboxylic acid to an oxidation reaction using a microorganism to obtain an (S)-sulfoxide product of (S)-benzhydrylsulfinyl carboxylic acid; and subjecting the (S)-sulfoxide product to an amidation reaction using a microorganism to obtain an (S)-sulfoxide-amide product of (+)-(S)-modafinil and a pharmaceutically acceptable carrier or excipient is provided.

In still another embodiment, a pharmaceutical composition includes (−)-(R)-modafinil, where the (−)-(R)-modafinil has been obtained by the method comprising subjecting benzhydrylsulfanyl carboxylic acid to an oxidation reaction using a microorganism to obtain an (R)-sulfoxide product of (R)-benzhydrylsulfinyl carboxylic acid; and subjecting the (R)-sulfoxide product to an amidation reaction using a microorganism to obtain an (R)-sulfoxide-amide product of (−)-(R)-modafinil and a pharmaceutically acceptable carrier or excipient is provided.

In still another embodiment, a method of treating a disease or disorder in a subject, includes administering to a subject in need thereof a therapeutically effective amount of racemic modafinil obtained by the method of subjecting benzhydrylsulfanyl carboxylic acid to an oxidation-amidation reaction using at least one microorganism to obtain a sulfoxide-amide product of racemic modafinil.

In still another embodiment, a method of treating a disease or disorder in a subject, includes administering to a subject in need thereof a therapeutically effective amount of (+)-(S)-modafinil obtained by the method of subjecting benzhydrylsulfanyl carboxylic acid to an oxidation reaction using a microorganism to obtain an (S)-sulfoxide product and subjecting the (S)-sulfoxide product to an amidation reaction using a microorganism to obtain an (S)-sulfoxide-amide product of (+)-(S)-modafinil.

In still another embodiment, a method of treating a disease or disorder in a subject, includes administering to a subject in need thereof a therapeutically effective amount of (−)-(R)-modafinil obtained by the method of subjecting benzhydrylsulfanyl carboxylic acid to an oxidation reaction using a microorganism to obtain an (R)-sulfoxide product and subjecting the (R)-sulfoxide product to an amidation reaction using a microorganism to obtain an (R)-sulfoxide-amide product of (−)-(R)-modafinil.

It is an object of the invention to provide a method of preparing modafinil with fewer steps than currently available.

Another object of the invention is to provide a method of preparing modafinil with enhanced yields.

Yet another object of the invention is to provide an environmentally friendly method of preparing modafinil.

Still another object of the invention is to provide pharmaceutical compositions comprising modafinil and a pharmaceutically acceptable carrier.

A further object of the invention is to provide a method of preparing modafinil in one vessel.

It is an object of the invention is to provide a method of preparing racemic modafinil.

Yet another object of the invention is to provide a method of preparing enantiomers of modafinil.

Still another object of the invention is to produce pharmaceutical compositions comprising an enantiomer of modafinil and a pharmaceutically acceptable carrier.

Yet another object of the invention is to provide a method of treating a disease or disorder in a subject which comprises administering to the subject a therapeutically effective amount of racemic modafinil or an enantiomer of modafinil produced by the methods of the present invention.

The means and methods of accomplishing one or more of these and/or other objectives will become apparent from the detailed description of the invention, which follows hereafter.

DETAILED DESCRIPTION OF THE PREFERRED EMBODIMENT

Current processes to make modafinil are hindered by their inability to synthesize a selective enantiomer of modafinil, lengthy multiple step processes, and generation of environmentally unfriendly waste. The present invention provides an efficient, environmentally friendly process that is able to selectively produce enantiomers of modafinil, in addition to racemic modafinil, in one reaction vessel.

The present invention relates to microbiological processes for preparing a racemic mixture of modafinil as well as specific enantiomers of modafinil, a (+)-(S)-enantiomer of modafinil or a (−)-(R)-enantiomer, having the general formula:

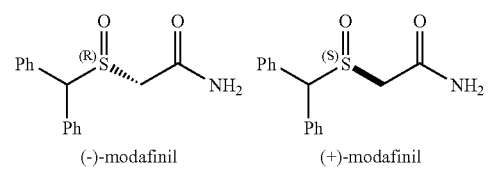

(−)-modafinil    (+)-modafinil wherein Ph is a phenyl group.

Modafinil is also known as (2-[(diphenylmethyl)sulfinyl] acetamide). Throughout the application, these phrases are used interchangeably. In one embodiment, the present invention relates to microbiological methods for preparing a racemic mixture of modafinil comprising subjecting benzhydrylsulfanyl carboxylic acid to an oxidation-amidation reaction using at least one microorganism to obtain a sulfoxide-amide product. In one aspect, the sulfoxide-amide product is a racemic mixture of modafinil.

In a second embodiment, the present invention provides methods for preparing an (S)-enantiomer of modafinil comprising subjecting benzhydrylsulfanyl carboxylic acid to an oxidation reaction using a microorganism to obtain a (S)-sulfoxide product, and subjecting the (S)-sulfoxide product to an amidation reaction using a microorganism to obtain an (S)-amide product. In one aspect the (S)-sulfoxide product is (S)-benzhydrylsulfinyl carboxylic acid. In another aspect the (S)-sulfoxide-amide product is the (+)-(S)-enantiomer of modafinil.

In a third embodiment, the present invention provides methods for preparing an (−)-(R)-enantiomer of modafinil comprising subjecting benzhydrylsulfanyl carboxylic acid to an oxidation reaction using a microorganism to obtain an (R)-sulfoxide product, and subjecting the (R)-sulfoxide product to an amidation reaction using a microorganism to obtain an (R)-amide product. In one aspect, the (R)-sulfoxide product is (R)-benzhydrylsulfinyl carboxylic acid. In one aspect, the (R)-sulfoxide-amide product is the (−)-(R)-enantiomer of modafinil.

The present inventors contemplate that the above methods may additionally include the preparation of benzhydrylsulfanyl carboxylic acid. Benzhydrylsulfanyl carboxylic acid may be prepared by any number of methods known to those skilled in the art, for example by reacting benzhydrol and thioglycolic acid to obtain benzhydrylsulfanyl carboxylic acid. The methods may also include the preparation of benzhydrylsulfinyl carboxylic acid, (S)-benzhydrylsulfinyl carboxylic acid or (R)-benzhydrylsulfinyl carboxylic acid.

The term "microorganism" as used herein includes any intact microorganism, for example, cells of the microorganism that substantially possess their inherent and/or induced, mechanical, physical and biochemical integrities, or suitable preparation therefrom, including, the microorganism washed free of, for example, fermentation medium, growth medium, culture broth, and the like, as the case may be; and the microorganism immobilized, for example, in a column, attached to beads or immobilized to cells. The microorganism employed in the methods of the invention can be in the form of fermentation broths, whole washed cells, concentrated cell suspensions, cell fragments or cell free extracts. See S. A. White and G. W. Claus (1982), J. Bacteriology, 150: 934-943 and S. Berezenko and R. J. Sturgeon (1991), Carbohydrate Research, 216: 505-509.

In addition, the "term" microorganism includes wild-type strains, mutant strains and recombinant strains, including those derived by the techniques of cell engineering such as cell fusion or by the techniques of genetic engineering such as gene manipulations, and enzyme extracts thereof insofar as the microorganism or extract thereof is capable of oxidizing benzhydrylsulfanyl carboxylic acid and/or amidating benzhydrylsulfinyl carboxylic acid to produce a racemic mixture of modafinil or a (+)-(S)-enantiomer of modafinil or a (−)-(R)-enantiomer of modafinil. According to the present invention, one may use naturally occurring or genetically engineered, recombinant, bacteria or mutant bacteria to carry out the oxidation or amidation reactions. Examples of bacteria suitable for genetic engineering include *E. coli, Alcaligenes latus, Alcaligenese eutrophus, Azotobacter, Pseudomonas putida*, and *Ralstonia eutropha*. Thus, a number of bacteria can be genetically engineered to include at least one gene or cDNA that encodes an enzyme or enzymatic peptide capable of carrying out an oxidation and/or amidation reaction. In one aspect, the genetically engineered bacteria expresses at least one oxygenase, wherein the oxygenase includes, without limitation, chloroperoxidases, monooxygenases, for example, cyclopentanone monooxygenase, cyclohexanone monooxygenase, alkane monooxygenase, or dioxygenases, for example, napthalene dioxygenase, and toluene dioxygenase. Examples of bacteria containing these enzymes include *E. coli* expressing naphthalene dioxygenase (NDO) from *Pseudomonas* sp. NCIB 9816-4, *E. coli* expressing toluene dioxygenase (TDO) from *Pseudomonas putida*, recombinant *E. coli* CPMO overexpressing cyclopentanone monooxygenase from *Pseudomonas* sp. NCIMB 9872, and recombinant *E. coli* CHMO overexpressing cyclohexanone monooxygenase from *Acinetobacter* sp. NCIMB 9871. Thus, the reactions may also be carried out by a microorganism, or cell fragment, or cell free extract thereof or by wild-type strains, mutant strains and recombinant strains or enzyme extracts thereof which is known or otherwise obtainable by one skilled in the relevant art and is able to accomplish the oxidation, amidation, or successive oxidation-amidation reactions in accordance with the present invention.

In one aspect of the present invention, the microorganism includes fungus, bacteria and/or yeast. In another aspect, the microorganism has the ability to successively oxidize benzhydrylsulfanyl carboxylic acid to benzhydrylsulfinyl carboxylic acid and amidate the benzhydrylsulfinyl carboxylic acid to produce a racemic mixture of modafinil. In another aspect of the present invention, the microorganism has the ability to stereo-selectively oxidize benzhydrylsulfanyl carboxylic acid to produce an (S)-sulfoxide product, (S)-benzhydrylsulfinyl carboxylic acid. In another aspect, the microorganism has the ability to stereo-selectively amidate (S)-benzhydrylsulfinyl carboxylic acid to produce an (+)-(S)-enantiomer of modafinil.

In another aspect, the microorganism has the ability to stereo-selectively oxidize benzhydrylsulfanyl carboxylic acid to produce an (R)-sulfoxide product, (R)-benzhydrylsulfinyl carboxylic acid. In another aspect, the microorganism has the ability to stereo-selectively amidate (R)-benzhydrylsulfinyl carboxylic acid to produce an (−)-(R)-enantiomer of modafinil.

In addition, the microorganisms according to this invention include bacteria that produce a racemic mixture of modafinil, those that selectively produce the (+)-(S)-enantiomer of modafinil or the (−)-(R)-enantiomer of modafinil through the oxidation of benzhydrylsulfanyl carboxylic acid and the amidation of benzhydrylsulfinyl carboxylic acid. The microorganism should be able to accomplish the oxidation of the sulfide of the benzhydrylsulfanyl carboxylic acid to sulfoxide generating the sulfoxide product benzhydrylsulfinyl carboxylic acid and the subsequent amidation of the carboxylic acid group on benzhydrylsulfinyl carboxylic acid to generate a sulfoxide-amide product, a racemic mixture of modafinil or an enantiomer of modafinil. The present inventors contemplate that the oxidation and amidation reactions may be carried out by the same or different microorganisms. For example, the oxidation-amidation reactions may be carried out by a microorganism of the same genus and species, such as *Amycolaptosis orientalis*, or alternately, the oxidation reaction may be carried out by a fungus such as *Beauveria bassiana* or bacteria *Rhodococcus rhodochrous*, and the amidation reaction carried out by bacteria *Bacillus subtilis* or *Amycolaptosis orientalis*.

Suitable microorganisms for use with the present invention may be found by growing a relatively large number of microorganisms in an appropriate nutrient medium which contains benzhydrylsulfanyl carboxylic acid and/or benzhydrylsulfinyl carboxylic acid and examining their ability to produce benzhydrylsulfinyl carboxylic acid or (S)- or (R)-benzhydrylsulfinyl carboxylic acid or racemic modafinil or its enantiomers respectively. The ability of a microorganism to catalyze the oxidation reaction according to the invention can be measured by a variety of means, including assaying with thin layer chromatography (TLC), high performance liquid chromatography (HPLC), or nuclear magnetic resonance (NMR) spectroscopy.

Microorganisms for use in the process of the invention are readily available from a variety of sources including but not limited to the American Type Culture Collection (ATCC), Rockville, Md.; the Agricultural Research Culture Collection (NRRL), Peoria, Ill.; Deutsche Sammlung Von Mikroorganismen (DSM), Federal Republic of Germany; and the Fermentation Research Institute (FRI), Japan: Japan Collection of Microorganisms (JCM), The Institute of Physical and Chemical Research; Institute of Applied Microbiology (LAM), The University of Tokyo; and NODAI Research Institute Culture Collection (NRIC), Tokyo University of Agriculture.

Alternatively, one skilled in the art can isolate required microorganisms from a variety of samples. Alternatively, a recombinant microorganism can be prepared by isolating or synthesizing the appropriate gene or cDNA for the oxidizing enzyme or amidating enzyme and inserting this gene or cDNA into another microorganism using standard literature techniques such as is disclosed in Molecular Cloning, A Laboratory Manual, 2nd Edition, J. Sambrook, E. F. Fritsch, T. Maniatis, eds, Vol. 1, 2, and 3, Cold Spring Harbor Laboratory Press (1989).

Enzyme activity may be obtained by growing the desired microorganism in a nutrient medium for a sufficient time. On separating the microbial cells from the fermentation broth through filtration or centrifugation, the enzyme activity is found mainly in the cells, rather than in the broth.

The present inventors also contemplate that new strains of microorganisms, for example, recombinant or mutant strains, may be employed in the present invention because, for example, they have improved properties relative to their respective parent strains, e.g., they produce more of the intermediate sulfoxide product benzhydrylsulfinyl carboxylic acid, or (S)- or (R)-benzhydrylsulfinyl carboxylic acid, or the sulfoxide-amide product of a racemic mixture of modafinil, an (+)-(S)-enantiomer of modafinil or an (−)-(R)-enantiomer of modafinil, they exhibit less unwanted intrinsic degradative activity of the starting material benzhydrylsulfanyl carboxylic acid or intermediate sulfoxide product, benzhydrylsulfinyl carboxylic acid, or (S)- or (R)-benzhydrylsulfinyl carboxylic acid, and/or the product, for example, a racemic mixture of modafinil, the (+)-(S)-enantiomer of modafinil or the (−)-(R)-enantiomer of modafinil which may be generated in the process of the present invention depending upon, for example, the particular microorganism chosen. In addition, new strains, mutants or recombinants of a microorganism, with more desirable properties, e.g., able to oxidize greater amounts of benzhydrylsulfanyl carboxylic acid or amidate greater amounts of benzhydrylsulfinyl carboxylic acid, or (S)- or (R)-benzhydrylsulfinyl carboxylic acid, faster compared to the parent strain, can also be used in the subject process, and these new strains may be made using known methods including, for example, standard mutagenesis and selection techniques, and recombinant methods including, for example, site-directed mutagenesis.

Standard mutagenesis methods include chemical mutagenesis with N-methyl-N'-nitrosoguanidine (Delic et al. (1970), Mutat. Res. 9:167), nitrous acid (Crueger and Crueger (1984), Biotechnology: A Textbook of Industrial Microbiology, p. 16, Sinauer Associates, Inc., Sunderland, Mass., USA) and irradiation with ultraviolet light (Thrum (1984), in Biotechnology of Industrial Antibiotics (Vandamme, ed.), Marcel Dekker, New York, pp. 373-374).

Additionally, microorganisms used in the present invention can be obtained by testing the microorganism's ability to produce a racemic mixture of modafinil, or for the selectivity to produce the (+)-(S)-enantiomer of modafinil or the (−)-(R)-enantiomer of modafinil. For example, when testing a microorganism's ability to oxidize and amidate in succession a substrate, for example, benzhydrylsulfanyl carboxylic acid, the substrate may be incubated with a microorganism under conditions sufficient for the oxidation-amidation reactions to occur and to yield an oxidized-amidated product, for example, a racemic mixture of modafinil, or the (+)-(S)-enantiomer of modafinil or the (−)-(R)-enantiomer of modafinil. Methods of preparing and selecting suitable substrates, for example, benzhydrylsulfanyl acetic acid, benzhydrylsulfanyl acetamide, as well as enantiomers, for example, (S)- or (R)-benzhydrylsulfinyl carboxylic acid are known to the skilled artisan. The resulting oxidized-amidated product may be determined or measured using HPLC. The optically active (S)- or (R)-oxidized-amidated product that is accumulated in the buffer may be measured using a chiral HPLC column. A microorganism can tested for its ability to successively oxidize and amidate a substrate and/or produce a mixture of optically active (S)- or (R)-oxidized-amidated product and used in the present invention. Thus, methods of the present invention also include identifying a microorganism that can oxidize and amidate in succession a substrate, for example, benzhydrylsulfanyl carboxylic acid, that includes contacting a test microorganism with an oxidation-amidation substrate and determining the oxidation-amidation of the substrate by measuring an oxidated-amidated product, for example, modafinil.

According to the present invention, when testing a microorganism's ability to oxidize a substrate, for example, benzhydrylsulfanyl carboxylic acid, the substrate may be incubated with a microorganism under conditions sufficient for the oxidation reaction to occur and to yield an oxidized product, for example, the sulfoxide product benzhydrylsulfinyl carboxylic acid. The resulting oxidized product may be determined or measured using HPLC and optical activity and purity measured using a chiral HPLC column. A microorganism can be tested for its ability to oxidize a substrate and/or produce an optically active (S) or (R)-oxidized product and used in the present invention. Accordingly, methods of the present invention also include identifying a microorganism that can oxidize a substrate, for example, benzhydrylsulfanyl carboxylic acid, that includes contacting a test microorganism with an oxidation substrate and determining the oxidation of the substrate by measuring an oxidated product, for example, benzhydrylsulfinyl carboxylic acid.

Similarly, when testing a microorganism's ability to amidate a substrate, for example, benzhydrylsulfinyl carboxylic acid, the substrate may be incubated with a microorganism under conditions sufficient for the amidation reaction to occur and to yield an amidated product, for example, a racemic mixture of modafinil, or the (+)-(S)-enantiomer of modafinil or the (−)-(R)-enantiomer of modafinil. The resulting amidated product may be determined or measured using HPLC and optical activity and purity measured using an optical resolution column or a chiral HPLC column. A microorganism can be tested for its ability to amidate a substrate and/or produce an optically active (S) or (R)-amidated product and used in the present invention. Thus, methods of the present invention also include identifying a microorganism that can amidate a substrate, for example, benzhydrylsulfinyl carboxylic acid, that includes contacting a test microorganism with an amidation substrate and determining the amidation of the substrate by measuring an amidated product, for example, a racemic mixture of modafinil, or the (+)-(S)-enantiomer of modafinil or the (−)-(R)-enantiomer of modafinil depending on the substrate used. "Optically active" herein refers to an (S) or (R)-oxidized-amidated product, (S)- or (R)-oxidized product, (S)- or (R)-amidated product, or (+)-(S) or (−)-(R)-enantiomer of modafinil that contains more of one optical isomer than it does of the other. According to the present invention, preferred optically active (+)-(S) or (−)-(R)-enantiomers of modafinil have an optical purity (enantiomeric excess; ee) of usually 40% ee or more, preferably 60% ee or more, more preferably 70% ee or more, and still more preferably 80% ee or more. The optical purity of an optically active (+)-(S) or (−)-(R)-enantiomer of modafinil can be determined using, for example, a chiral chromatographic HPLC column. "Optical isomers" of the present invention are generally referred to as "optically active substances" or "enantiomers".

Examples of Microorganisms:

Microorganisms capable of successively oxidizing and amidating a substrate, for example, benzhydrylsulfanyl carboxylic acid, to convert it to the corresponding sulfoxide-amide product, for example, modafinil, include bacteria belonging to the genus *Abiotrphia, Achromobacter, Acidovorax, Acinetobacter, Aerococcusm Aeromonas, Agrobacterium, Alcaligenes, Alishwanella, Alloicoccis, Ammoniphilus, Amphibacillus, Amycolaptosis, Aneurinbacillus, Arcanobacterium, Arthrobacter, Bacillus, Balneatrix, Bergeyella, Brenneria, Brevibacillus, Brevibacterium, Brevundimonas, Budvicia, Burkholderia, Buttiauxella, Cedecea, Cellulomonas, Cellulosimicrobium, Chromobacterium, Chrysobacterium, Citrobacter, Comamonas, Cornynebacterium, Curtobacterium, Delftia, Dermabacter, Dermacoccus, Dolosicoccus, Edwardsiella, Empedobacter, Enterobacter, Enterococcus, Erwinia, Erysipelothrix, Escherichia, Ewingella, Exiguobacterium, Facklamia, Flavimonas, Flavobacterium, Gemella, Gllobicatella, Granulicatella, Hafnia, Halomonas, Helcoccus, Klebsiella, Kluyvera, Kocuria, Kytococcus, Lactococcus, Leclercia, Legionella, Leifsonia, Leminorella, Leuconistic, Listeria, Macrococcus, Methylobacterium, Microbacterium, Micrococcus, Micropolyspora, Moellerella, Moraxella, Morganella, Mycobacterium, Myoides, Nresterenkonia, Nocardia, Nocardiopsism Obesumbacterium, Ochrobacterium, Oerskovia, Olligella, Paenibacillus, Pandoraea, Pantoea, Pasteurella, Pectobacterium, Pediococcus, Pedobacter, Photohabdus, Plesiomonas, Pragia, Proteus, Providencia, Pseudomonas, Psychobacter, Rahnella, Ralstonia, Raoutella, Rhizobium, Rhodococcus, Roseomonas, Rothia, Saccharomonospora, Sacchraopolyspora, Salmonella, Serratia, Shewanella, Sphingobacterium, Sphingomonas, Sodalis, Staphylococcus, Stenotrophomonas, Streptococcus, Streptomyces, Tatumella, Thermoactinomyces, Thermobacillus, Trabulsiella, Vagococcus, Virgibacillus, Weeksella, Xenorhabdus, Yersinia,* and *Yokenella.*

Microorganisms capable of successively oxidizing and amidating a substrate, for example, benzhydrylsulfanyl carboxylic acid, to convert it to the corresponding sulfoxide-amide product, for example, modafinil, include fungus belonging to the genus *Absidia, Acremonium, Alternaria, Amblysporium, Aphanocladium, Arthrinium, Arthrobotrys, Arthroderma, Arthographis, Ascotricha, Aspergillus, Asteromyces, Aureibasidium, Basipetospora, Beauveria, Bipolaris, Bispora, Botryosporium, Botrytis, Byssochlamys, Caldariomyces, Calcarisporium, Cephaliophora, Ceratocystis, Cerebella, Cercospora, Chaetmium, Chromelosporium, Chrysinilia, Chrysosporium, Cladiophialophora, Cladosporium, Collectrichum, Cunninghamella, Curvulvaria, Cylindrocarpon, Clylindrocladium, Dicyma, Drechslera, Echinobotryum, Emericella, Emmonsia, Epicoccum, Epidermophyton, Eupenicilium, Eurotium, Exophiala, Exserihilum, Fusarium, Geomyces, Geotrichum, Gliocladium (Clonobotrys), Gliomastix, Gonatobotryum, Graphium, Helminthosporium, Hormographiella, Humicola, Hyalodendron, Lecythophora, Leptographium, Leptosphaeria, Leptosphaerulina, Malbranchea, Memnoniella, Metarhizium, Microspaeropsis, Microsporum, Monodictys, Mortierella, Mucor, Mycotypha, Myrothecium, Nectria, Neosartorya, Nigrospora, Oedocephalum, Oidiodendron, Ophiostoma, Paecilomyces, Papulaspora, Penicillium, Periconia, Pestalotiopsis, Phialocephala, Philophora, Phoma, Phragmocephala, Pithomyces, Polypaecilum, Polythricium, Rhinocladiella, Rhizomucor, Rhizopus, Rhodotortula, Scolecobasidium (Ochroconis), Scopulariopsis, Scytalidium, Sepedonium, Sordaria, Spegazzinia, Sporobolomyces, Sporothrix, Sporotrichum, Stachybotrys, Staphylotrichum, Stemphylium, Syncephalastrum, Taeniolella, Talaromyces, Tetraploa, Thamnidium, Thysanophora, Tilletiopsis, Torula, Torulomyces, Trichiconiella, Trichoderma, Trichophyton, Trichothecium, Tritirachium, Ulocladium, Verticillium, Verticicladiella, Wallemia,* and *Xeromyces.*

Microorganisms capable of oxidizing a substrate, for example, benzhydrylsulfanyl carboxylic acid, to convert it to the corresponding sulfoxide product, for example, benzhydrylsulfinyl carboxylic acid, include those bacteria belonging to the genus *Abiotrphia, Achromobacter, Acidovorax, Acinetobacter, Aerococcusm Aeromonas, Agrobacterium, Alcaligenes, Alishwanella, Alloicoccis, Ammoniphilus, Amphibacillus, Amycolaptosis, Aneurinbacillus, Arcanobacterium, Arthrobacter, Bacillus, Balneatrix, Bergeyella, Brenneria, Brevibacillus, Brevibacterium, Brevundimonas, Budvicia, Burkholderia, Buttiauxella, Cedecea, Cellulomonas, Cellulosimicrobium, Chromobacterium, Chrysobacterium, Citrobacter, Comamonas, Cornynebacterium, Curtobacterium, Delftia, Dermabacter, Dermacoccus, Dolosicoccus, Edwardsiella, Empedobacter, Enterobacter, Enterococcus, Erwinia, Erysipelothrix, Escherichia, Ewingella, Exiguobacterium, Facklamia, Flavimonas, Flavobacterium, Gemella, Gllobicatella, Granulicatella, Hafnia, Halomonas, Helcoccus, Klebsiella, Kluyvera, Kocuria, Kytococcus, Lactococcus, Leclercia, Legionella, Leifsonia, Leminorella, Leuconistic, Listeria, Macrococcus, Methylobacterium, Microbacterium, Micrococcus, Micropolyspora, Moellerella, Moraxella, Morganella, Mycobacterium, Myoides, Nresterenkonia, Nocardia, Nocardiopsism Obesumbacterium, Ochrobacterium, Oerskovia, Olligella, Paenibacillus, Pandoraea, Pantoea, Pasteurella, Pectobacterium, Pediococcus, Pedobacter, Photohabdus, Plesiomonas, Pragia, Proteus, Providencia, Pseudomonas, Psychobacter, Rahnella, Ralstonia, Raoutella, Rhizobium, Rhodococcus, Roseomonas, Rothia, Saccharomonospora, Sacchraopolyspora, Salmonella, Serratia, Shewanella, Sphingobacterium, Sphingomonas, Sodalis, Staphylococcus, Stenotrophomonas, Streptococcus, Streptomyces, Tatumella, Thermoactinomyces, Thermobacillus, Trabulsiella, Vagococcus, Virgibacillus, Weeksella, Xenorhabdus, Yersinia,* and *Yokenella.*

Microorganisms capable of oxidizing a substrate, for example, benzhydrylsulfanyl carboxylic acid, to convert it to the corresponding sulfoxide product, for example, benzhydrylsulfinyl carboxylic acid, include those fungus belonging to the genus *Absidia, Acremonium, Alternaria, Amblysporium, Aphanocladium, Arthrinium, Arthrobotrys, Arthroderma, Arthographis, Ascotricha, Aspergillus, Asteromyces, Aureibasidium, Basipetospora, Beauveria, Bipolaris, Bispora, Botryosporium, Botrytis, Byssochlamys, Caldariomyces, Calcarisporium, Cephaliophora, Ceratocystis, Cerebella, Cercospora, Chaetmium, Chromelosporium, Chrysinilia, Chrysosporium, Cladiophialophora, Cladosporium, Collectrichum, Cunninghamella, Curvulvaria, Cylindrocarpon, Clylindrocladium, Dicyma, Drechslera, Echinobotryum, Emericella, Emmonsia, Epicoccum, Epidermophyton, Eupenicilium, Eurotium, Exophiala, Exserihilum, Fusarium, Geomyces, Geotrichum, Gliocladium (Clonobotrys), Gliomastix, Gonatobotryum, Graphium, Helminthosporium, Hormographiella, Humicola, Hyalodendron, Lecythophora, Leptographium, Leptosphaeria, Leptosphaerulina, Malbranchea, Memnoniella, Metarhizium, Microspaeropsis, Microsporum, Monodictys, Mortierella, Mucor, Mycotypha,*

*Myrothecium, Nectria, Neosartorya, Nigrospora, Oedocephalum, Oidiodendron, Ophiostoma, Paecilomyces, Papulaspora, Penicillium, Periconia, Pestalotiopsis, Phialocephala, Philophora, Phoma, Phragmocephala, Pithomyces, Polypaecilum, Polythricium, Rhinocladiella, Rhizomucor, Rhizopus, Rhodotortula, Scolecobasidium (Ochroconis), Scopulariopsis, Scytalidium, Sepedonium, Sordaria, Spegazzinia, Sporobolomyces, Sporothrix, Sporotrichum, Stachybotrys, Staphylotrichum, Stemphylium, Syncephalastrum, Taeniolella, Talaromyces, Tetraploa, Thamnidium, Thysanophora, Tilletiopsis, Torula, Torulomyces, Trichiconiella, Trichoderma, Trichophyton, Trichothecium, Tritirachium, Ulocladium, Verticillium, Verticicladiella, Wallemia,* and *Xeromyces.*

Microorganisms capable of amidating a substrate, for example, benzhydrylsulfinyl carboxylic acid, to convert it to the corresponding sulfoxide-amide product, for example, modafinil, include those bacteria belonging to the genus *Abiotrphia, Achromobacter, Acidovorax, Acinetobacter, Aerococcusm Aeromonas, Agrobacterium, Alcaligenes, Alishwanella, Alloicoccis, Ammoniphilus, Amphibacillus, Amycolaptosis, Aneurinbacillus, Arcanobacterium, Arthrobacter, Bacillus, Balneatrix, Bergeyella, Brenneria, Brevibacillus, Brevibacterium, Brevundimonas, Budvicia, Burkholderia, Buttiauxella, Cedecea, Cellulomonas, Cellulosimicrobium, Chromobacterium, Chrysobacterium, Citrobacter, Comamonas, Cornynebacterium, Curtobacterium, Delftia, Dermabacter, Dermacoccus, Dolosicoccus, Edwardsiella, Empedobacter, Enterobacter, Enterococcus, Erwinia, Erysipelothrix, Escherichia, Ewingella, Exiguobacterium, Facklamia, Flavimonas, Flavobacterium, Gemella, Gllobicatella, Granulicatella, Hafnia, Halomonas, Helcoccus, Klebsiella, Kluyvera, Kocuria, Kytococcus, Lactococcus, Leclercia, Legionella, Leifsonia, Leminorella, Leuconistic, Listeria, Macrococcus, Methylobacterium, Microbacterium, Micrococcus, Micropolyspora, Moellerella, Moraxella, Morganella, Mycobacterium, Myoides, Nresterenkonia, Nocardia, Nocardiopsism Obesumbacterium, Ochrobacterium, Oerskovia, Olligella, Paenibacillus, Pandoraea, Pantoea, Pasteurella, Pectobacterium, Pediococcus, Pedobacter, Photohabdus, Plesiomonas, Pragia, Proteus, Providencia, Pseudomonas, Psychobacter, Rahnella, Ralstonia, Raoutella, Rhizobium, Rhodococcus, Roseomonas, Rothia, Saccharomonospora, Sacchraopolyspora, Salmonella, Serratia, Shewanella, Sphingobacterium, Sphingomonas, Sodalis, Staphylococcus, Stenotrophomonas, Streptococcus, Streptomyces, Tatumella, Thermoactinomyces, Thermobacillus, Trabulsiella, Vagococcus, Virgibacillus, Weeksella, Xenorhabdus, Yersinia,* and *Yokenella.*

Microorganisms capable of amidating a substrate, for example, benzhydrylsulfinyl carboxylic acid, to convert it to the corresponding sulfoxide-amide product, for example, modafinil, include those fungus belonging to the genus *Absidia, Acremonium, Alternaria, Amblysporium, Aphanocladium, Arthrinium, Arthrobotrys, Arthroderma, Arthographis, Ascotricha, Aspergillus, Asteromyces, Aureibasidium, Basipetospora, Beauveria, Bipolaris, Bispora, Botryosporium, Botrytis, Byssochlamys, Caldariomyces, Calcarisporium, Cephaliophora, Ceratocystis, Cerebella, Cercospora, Chaetmium, Chromelosporium, Chrysinilia, Chrysosporium, Cladiophialophora, Cladosporium, Collectrichum, Cunninghamella, Curvulvaria, Cylindrocarpon, Clylindrocladium, Dicyma, Drechslera, Echinobotryum, Emericella, Emmonsia, Epicoccum, Epidermophyton, Eupenicillium, Eurotium, Exophiala, Exserihilum, Fusarium, Geomyces, Geotrichum, Gliocladium (Clonobotrys), Gliomastix, Gonatobotryum, Graphium, Helminthosporium, Hormographiella, Humicola, Hyalodendron, Lecythophora, Leptographium, Leptosphaeria, Leptosphaerulina, Malbranchea, Memnoniella, Metarhizium, Microspaeropsis, Microsporum, Monodictys, Mortierella, Mucor, Mycotypha, Myrothecium, Nectria, Neosartorya, Nigrospora, Oedocephalum, Oidiodendron, Ophiostoma, Paecilomyces, Papulaspora, Penicillium, Periconia, Pestalotiopsis, Phialocephala, Philophora, Phoma, Phragmocephala, Pithomyces, Polypaecilum, Polythricium, Rhinocladiella, Rhizomucor, Rhizopus, Rhodotortula, Scolecobasidium (Ochroconis), Scopulariopsis, Scytalidium, Sepedonium, Sordaria, Spegazzinia, Sporobolomyces, Sporothrix, Sporotrichum, Stachybotrys, Staphylotrichum, Stemphylium, Syncephalastrum, Taeniolella, Talaromyces, Tetraploa, Thamnidium, Thysanophora, Tilletiopsis, Torula, Torulomyces, Trichiconiella, Trichoderma, Trichophyton, Trichothecium, Tritirachium, Ulocladium, Verticillium, Verticicladiella, Wallemia,* and *Xeromyces.*

The present inventors also contemplate that species from the genera thereof may be used in the present invention provided that the microorganisms are capable of accomplishing the oxidation-amidation, oxidation or amidation reactions. In one embodiment, a racemic mixture of modafinil is prepared by subjecting benzhydrylsulfanyl carboxylic acid to an oxidation-amidation reaction using at least one microorganism to obtain a sulfoxide-amide product, for example, a racemic mixture of modafinil or an enantiomer of modafinil. In another embodiment, the microorganism is *Amycolaptosis orientalis*. Further, the present invention also includes microorganisms that are capable of carrying out the oxidation and/or amidation reactions in an enantioselective manner.

In another embodiment, a method of preparing (S)-enantiomer of modafinil comprises subjecting benzhydrylsulfanyl carboxylic acid to an oxidation reaction using a microorganism to obtain an (S)-sulfoxide product; and subjecting the (S)-sulfoxide product to an amidation reaction using a microorganism to obtain an (S)-sulfoxide-amide product. In another embodiment, the microorganism capable of carrying out the oxidation reaction to obtain a (S)-sulfoxide product includes, but is not limited to, *Beauveria bassiana, Microsporum gypseum, Mortierella isabellina, Caldariomyces fumago, Mortierella elongata, Helminthosporium* sp., *Amycolaptosis orientalis, Thamnidium elegans,* and genetically engineered microorganisms, for example, bacteria, that express an oxygenase.

In another embodiment, the microorganism capable of carrying out the amidation reaction to obtain the (S)-enantiomer of modafinil includes, but is not limited to, *Bacillus subtilis* and *Amycolaptosis orientalis*.

In another embodiment, a method of preparing an (R)-enantiomer of modafinil comprises subjecting benzhydrylsulfanyl carboxylic acid to an oxidation reaction using a microorganism to obtain an (R)-sulfoxide product and subjecting the (R)-sulfoxide product to an amidation reaction using a microorganism to obtain an (R)-sulfoxide-amide product. In another embodiment, the microorganism capable of carrying out an oxidation reaction to obtain an (R)-sulfoxide product includes, but is not limited to, *Rhodococcus rhodochrous, Shingomonas* sp., *Cylindrocarpon radicicola,* and genetically engineered microorganisms, for example, bacteria, that express an oxygenase. In another embodiment, the microorganism capable of carrying out an amidation reaction to obtain an (R)-enantiomer of modafinil includes, but is not limited to, *Bacillus subtilis* and *Amycolaptosis orientalis*.

Any suitable method of contacting the substrate, for example, benzhydrylsulfanyl carboxylic acid and/or benzhydrylsulfinyl carboxylic acid, with the microorganism in its various embodiments, whole (intact), cellular extracts or fragments, immobilized, may be used in the oxidation or amidation reactions of the present invention including, for example, shaking, stirring and aerating.

The substrate benzhydrylsulfanyl carboxylic acid and/or benzhydrylsulfinyl carboxylic acid may be contacted with the microorganism in any suitable order. For example, the substrate benzhydrylsulfanyl carboxylic acid and/or benzhydrylsulfinyl carboxylic acid may be added to a medium, such as a culture broth, comprising the microorganism, free or immobilized, or some combination thereof; or the medium may comprise the substrate benzhydrylsulfanyl carboxylic acid and/or benzhydrylsulfinyl carboxylic acid and the microorganism may then be added to such medium; or the substrate benzhydrylsulfanyl carboxylic acid and/or benzhydrylsulfinyl carboxylic acid and the microorganism may be added together to such medium; or either the substrate benzhydrylsulfanyl carboxylic acid and/or benzhydrylsulfinyl carboxylic acid or the microorganism may be added to a suitable solvent comprising the other; or the substrate benzhydrylsulfanyl carboxylic acid and/or benzhydrylsulfinyl carboxylic acid may be adsorbed to a resin; and the like. Those skilled in the art will understand from the description provided herein how to modify any part of the processes as so desired.

Any suitable duration of growth of the microorganism (i.e., fungus or bacterium), contacting of the microorganism with substrate benzhydrylsulfanyl carboxylic acid and/or benzhydrylsulfinyl carboxylic acid, and incubation of substrate benzhydrylsulfanyl carboxylic acid and/or benzhydrylsulfinyl carboxylic acid with the microorganism may be used in the present invention.

There are no particular limitations to the different conditions in the culturing of the microorganisms, and the methods that are ordinarily used may be carried out, where bacteria, fungi, and yeast are cultured in suitable media, respectively. General growth conditions for culturing the particular organisms may be obtained from depositories and from texts known in the art such as Bergey's Manual of Systematic Bacteriology, Vol. 1, Williams and Wilkins, Baltimore/London (1984), N. R. Krieg, ed.

The nutrient medium for the growth of any oxidizing microorganism and/or amidating microorganism should contain sources of assimilable carbon and nitrogen, as well as mineral salts. Suitable sources of assimilable carbon and nitrogen include, but are not limited to, complex mixtures, such as those constituted by biological products of diverse origin, for example soy bean flour, cotton seed flour, lentil flour, pea flour, soluble and insoluble vegetable proteins, corn steep liquor, yeast extract, yeast and casein hydrolysates, peptones and meat extracts. Any sources may be used for the nitrogen source of the medium as long as the microorganisms can utilize them. Additional sources of nitrogen include simple, synthesizable organic and inorganic compounds such as ammonium salts, alkali nitrates, amino acids, nitrates, such as ammonium chloride, ammonium sulphate, sodium nitrate and potassium nitrate. Any sources may be used for the carbon source of the medium as long as the microorganisms can utilize them. Specifically, there may be used sugars such as glucose, fructose, sucrose, maltose, mannose, glycerin, millet jelly, molasses, dextrin, starch, and sorbitol; alcohols such as methanol, ethanol, and glycerol; organic acids such as fumaric acid, citric acid, acetic acid, and propionic acid and their salts; hydrocarbons such as paraffin; and mixtures of the foregoing. Nutrition sources may also be added appropriately to the medium, which are used in culturing, including inorganic salts, the salts of minute metals, and vitamins. Generally, the nutrient medium may include, but is not limited to, the following ions: $Mg^{++}$, $Na^+$, $K^+$, $Ca^{++}$, $NH_4^+$, $Cl^-$, $SO_4^{--}$, $PO_4^{---}$ and $NO_3^-$ and also ions of the trace elements such as Cu, Fe, Mn, Mo, Zn, Co and Ni. The preferred source of these ions are mineral salts. There may also be added to the medium, a substance for inducing the activity of a microorganism and/or a buffer substance effective to maintain pH.

The culture may be used directly for the oxidation and/or amidation of benzhydrylsulfanyl carboxylic acid and benzhydrylsulfinyl carboxylic acid respectively. Alternately, the supernatants may be removed through filtration or centrifugation, and the microbial cells containing the major portion of the enzyme used for the reaction. In one aspect, the microbial cells can be used directly as a whole cell enzyme. The cell extract obtained after disruption of whole cells and centrifugation may also be used as an enzyme source with or without freeze drying. The immobilized enzyme can also be used for a continuous process or repetitively used in a batch reaction. The immobilized enzyme can be prepared through the adsorption of the enzyme of the cell extract on silicate materials such as bentonite, celite, diatomaceous earth, kaolin, silica gel or other materials such as activated carbon or alumina. The entrappment of whole cells in acrylamide gel with or without defatting the cells by treatment with acetone can be used for the preparation of the immobilized enzyme.

The oxidation of benzhydrylsulfanyl carboxylic acid and amidation of benzhydrylsulfinyl carboxylic acid can be carried out at any pH and temperature that allows for the production of benzhydrylsulfinyl carboxylic acid and the thus produced modafinil in a racemic mixture or in an enantiomeric form. For example, the oxidation and amidation reactions may be preformed at 27° C. in a temperature-controlled room with the pH of the reaction being adjusted to 7 at the beginning of the reaction and decreasing to about 6.4 at the end of the reaction.

One method for the preparation of the selected fungus comprises inoculating the fungus from the frozen vegetative cell or spore stock culture such as described above into a flask or a glass tube with a metal closure containing a growth medium (containing an aliquot from a sterile solution which includes Tween 80, glycerol and distilled water) whose composition is described in more detail below. The fermentation is carried out at temperatures ranging from about 22° C. to about 32° C., and preferably at about 29° C., with suitable shaking, preferably from about 200 rpm to about 220 rpm, and most preferably, at about 210 rpm. Where so desired, the pH of the growth medium can be maintained by the use of suitable buffers incorporated into the fermentation medium and/or periodically adjusted by addition of either base or acid as so required. A preferred pH range is from about pH 6 to about pH 7. Selection of the reaction pH depends upon the relative enzyme activity at the selected pH and the type of the desired product.

In embodiments of the present invention wherein the microorganism is a fungus, the substrate, benzhydrylsulfanyl carboxylic acid and/or benzhydrylsulfinyl carboxylic acid, may be added in any suitable way as described above and present in the oxidation and amidation reactions at a concentration range for the total amount of substrate, benzhydrylsulfanyl carboxylic acid and/or benzhydrylsulfinyl carboxylic acid, is from about 0.01 g/L to about 2.5 g/L, and in one aspect the range is from about 0.1 g/L to about 2.0 g/L, and preferably about 1.0 g/1 L. The cell density for the fungal cultures of the present invention is from about 40 to about 50 g wet cell weight/L of media, and preferably between 42.5 g to 47.5 g wet weight cells/L of media or 4.25 g to 4.75 g dry cell weight to L of media.

One method for the preparation of the selected bacterium comprises inoculating the bacteria from a frozen stock culture prepared as is known in the art (about a 17% glycerol stock) into a flask or a glass tube with a metal closure or a fermentor containing a growth medium (containing an aliquot from a sterile solution which includes Tween 80, glycerol and distilled water) whose composition is described in more detail below. The growth is carried out at temperatures ranging from about 20° C. to about 40° C., and preferably at temperatures ranging from about 25° C. to about 32° C., with suitable shaking, preferably from about 200 rpm to about 220 rpm, and most preferably, at about 210 rpm. Where so desired, the pH of the growth medium can be maintained by the use of suitable buffers incorporated into the fermentation medium and/or periodically adjusted by addition of either base or acid as so required. A preferred inoculum is from about 1% to about 20% v/v (inoculum/medium). A preferred pH range is from about pH 6 to about pH 8.

In an embodiment of the present invention wherein the microorganism is a bacterium, the substrate, benzhydrylsulfanyl carboxylic acid and/or benzhydrylsulfinyl carboxylic acid, may be added in any suitable way as described previously and present at a concentration range for the total amount of substrate, benzhydrylsulfanyl carboxylic acid and/or benzhydrylsulfinyl, is from about 0.01 g/L to about 15 g/L, and a particularly preferred range is from about 0.1 g/L to about 15 g/L. In embodiments of the present invention wherein the bacterium is selected from the genera described above, a preferred concentration range of substrate is from about 0.1 g/L to about 15 g/L. One skilled in the art would be familiar with such methods used to determine the appropriate cell density by measuring optical density or measuring cell mass using, for example, gravimetry.

In another aspect of the present invention wherein the microorganism is a bacterium, the microorganism may be cultured in a growth medium in a flask, and an inducer is added to such growth medium prior to or along with the contacting of the microorganism with the substrate, for example, benzhydrylsulfanyl carboxylic acid and/or benzhydrylsulfinyl carboxylic acid, and incubated in such growth medium for a period of time sufficient for the substantial completion of such induction. The cells of the induced bacteria are collected by centrifuging the contents of the flask, removing, e.g., decanting, the spent growth medium and the inducer, washing the cell pellet and resuspending the pellet in an aqueous medium, such as DPBS (Biowhittaker), prior to the contacting of said substrate benzhydrylsulfanyl carboxylic acid and/or benzhydrylsulfinyl carboxylic acid with the bacteria. As would be understood by those skilled in the art from the present disclosure and from the aforementioned articles and patents (e.g., U.S. Pat. No. 5,236,832), the inducer concentration is usually selected so that it is lower than the minimal inhibitory concentration of the enzymes responsible for the oxidation. See also, Claus and Walker, J. Gen. Microbiol., 36:107-122 (1964). Suitable inducers include, but are not limited to, toluene, xylene or cymene.

In another aspect of the present invention wherein the microorganism is a bacterium, or a suitable recombinant mutant thereof, and the microorganism is cultured in a growth medium in a flask, the inducer is added to such growth medium prior to or along with the contacting of the microorganism with the substrate, for example, benzhydrylsulfanyl carboxylic acid, and incubated in such growth medium for a period of time sufficient for the substantial completion of such induction. The cells of the induced microorganism are collected by centrifuging the contents of the flask, removing, e.g., decanting, the spent growth medium (and thus the subject inducer), washing the cell pellet and resuspending the pellet in an aqueous medium, such as DPBS (Biowhittaker), prior to the contacting of said substrate with said microorganism.

It should be noted that reference to particular buffers, media, reagents, contacting or culture conditions, amount of substrate, amount of inducer where used, and the like, in any part of the present disclosure is not intended to be limiting, but should be read to include all such related materials that those of ordinary skill in the art would recognize as being of interest or value in the particular context in which the discussion herein is presented. For example, it is often possible to substitute one buffer system or culture medium for another, such that a different but known way is used to achieve the same goals as those to which the use of a suggested method, material or composition is directed.

The degree of enzyme reaction can be determined by thin layer chromatography (TLC) using Eastman Chromagram Sheet No. 13181 and a developing solvent of chloroform/acetone (1:1) mixture. The time-dependent formation of the benzhydrylsulfinyl carboxylic acid, or (S)- or (R)-benzhydrylsulfinyl carboxylic acid, and/or modafinil (a racemic mixture of modafinil, (+)-(S)-enantiomer of modafinil or (−)-(R)-enantiomer of modafinil) in the culture medium can be followed either by thin layer chromatography or high performance liquid chromatography (HPLC). The optical activity and optical purity of the modafinil produced according to the present invention may be determined using high performance liquid chromatography (HPLC) and/or a chiral HPLC column, thus allowing one to determine whether the modafinil produced is a racemic mixture of modafinil, an (+)-(S)-enantiomer of modafinil or an (−)-(R)-enantiomer of modafinil.

As described above, the microorganism employed in the process of the invention may be in the form of fermentation broths, whole washed cells, concentrated cell suspensions, cell fragments or cell free extracts, and immobilized cells. (S. A. White and G. W. Claus (1982), J. Bacteriology, 150: 934-943 and S. Berezenko and R. J. Sturgeon (1991), Carbohydrate Research, 216: 505-509).

Concentrated washed cell suspensions can be prepared as follows: the microorganisms are cultured in a suitable nutrient solution, harvested (for example by centrifuging) and suspended in a smaller volume (in salt or buffer solutions, such as physiological sodium chloride solution or aqueous solutions of potassium phosphate, sodium acetate, sodium maleate, magnesium sulfate, or simply in tap water, distilled water or nutrient solutions). Benzhydrylsulfanyl carboxylic acid and/or benzhydrylsulfinyl carboxylic acid is then added to a cell suspension of this type and the oxidation reaction according to the invention is carried out under the conditions described.

The conditions for oxidation of benzhydrylsulfanyl carboxylic acid and amidation of benzhydrylsulfinyl carboxylic acid in growing microorganism cultures or cell fragments or cell free extracts are similar to those for carrying out the process according to the invention with concentrated cell suspensions. In particular the temperature range is from about 0° C. to about 45° C. and the pH range is from about 2 to about 10. There are no special nutrients necessary in the process of the invention. More importantly, washed or immobilized cells, cell fragments or cell free extracts can simply be added to a solution of benzhydrylsulfanyl carboxylic acid and/or benzhydrylsulfinyl carboxylic acid, without any nutrient medium present.

The process of the invention can also be carried out with cell fragments or cell free extracts prepared from bacteria. The cell free extracts can be crude extracts, such as obtained by conventional digestion of microorganism cells. Methods to break up cells include, but are not limited to, mechanical disruption, physical disruption, chemical disruption, and enzymatic disruption. Such means to break up cells include ultrasonic treatments, passages through French pressure cells, grindings with quartz sand, autolysis, heating, osmotic shock, alkali treatment, detergents, or repeated freezing and thawing.

If the process according to the invention is to be carried out with partially purified cell fragments or cell free extract preparations, the methods of protein chemistry, such as ultracentrifuging, precipitation reactions, ion exchange chromatography or adsorption chromatography, gel filtration or electrophoretic methods, can be employed to obtain such preparations. In order to carry out the reaction according to the invention with fractionated cell free extracts, it may be necessary to add to the system additional reactants such as, physiological or synthetic electron acceptors, like $NAD^+$, $NADP^+$, methylene blue, dichlorophenolindophenol, tetrazolium salts and the like. When these reactants are used, they can be employed either in equimolar amounts (concentrations which correspond to that of the benzhydrylsulfanyl carboxylic acid and/or benzhydrylsulfinyl carboxylic acid) or in catalytic amounts (concentrations which are markedly below the chosen concentration of benzhydrylsulfanyl carboxylic acid and/or benzhydrylsulfinyl carboxylic acid). If, when using catalytic amounts, it is to be ensured that the process according to the invention is carried out approximately quantitatively, a system which continuously regenerates the reactant which is present only in a catalytic amount must also be added to the reaction mixture.

The optically active enantiomers of modafinil produced by the present invention may be purified by conventional separation/purification means. For example, directly from the reaction solution or after the bacterial or fungal cells are separated, optically active enantiomers of modafinil can be obtained by being subjected to normal purification methods such as membrane separation or extraction with an organic solvent (e.g., toluene and chloroform), column chromatography, concentration at reduced pressure, distillation, recrystallization, and crystallization.

The methods of the present invention optionally comprises the isolation of the desired intermediate benzhydrylsulfinyl carboxylic acid or the product of a racemic mixture of modafinil, the (+)-(S)-enantiomer of modafinil or the (−)-(R)-enantiomer of modafinil using any suitable method. The product modafinil may be isolated as described below from the medium in which the oxidation and/or amidation process was performed and, more specifically, from any intermediate compounds which may have been produced but not completely converted to the product, for example, a racemic mixture of modafinil, (+)-(S)-enantiomer of modafinil or (−)-(R)-enantiomer of modafinil depending upon, e.g., the microorganism selected and the conditions of incubation.

Any suitable methods for isolating and/or purifying any of the intermediates or the desired product of the subject process may be used in the present invention including filtration, extraction, crystallization, column chromatography, thin-layer chromatography, preparative low pressure liquid chromatography, HPLC, resin adsorption, or any suitable combination of such methods.

The methods of the present invention are readily carried out. The modafinil produced by the present methods, for example, a racemic mixture of modafinil, (+)-(S)-enantiomer of modafinil, or (−)-(R)-enantiomer of modafinil, may be used in a pharmaceutical composition. In one embodiment, a pharmaceutical composition comprises a racemic mixture of modafinil, wherein said modafinil has been obtained by subjecting benzhydrylsulfanyl carboxylic acid to an oxidation-amidation reaction using at least one microorganism to obtain a sulfoxide-amide product; and a pharmaceutically acceptable carrier or excipient. In one aspect, the oxidation and amidation reactions are successive and carried out by the same microorganism.

In another embodiment, a pharmaceutical composition comprises (+)-(S)-modafinil, wherein said (+)-(S)-modafinil has been obtained by subjecting benzhydrylsulfanyl carboxylic acid to an oxidation reaction using a microorganism to obtain an (S)-sulfoxide product; and subjecting the (S)-sulfoxide product to an amidation reaction using a microorganism to obtain an (S)-sulfoxide-amide product, and a pharmaceutically acceptable carrier or excipient.

In another embodiment, a pharmaceutical composition comprises (−)-(R)-modafinil, wherein said (−)-(R)-modafinil has been obtained by subjecting benzhydrylsulfanyl carboxylic acid to an oxidation reaction using a microorganism to obtain an (R)-sulfoxide product; and subjecting the (R)-sulfoxide product to an amidation reaction using a microorganism to obtain an (R)-sulfoxide-amide product; and a pharmaceutically acceptable carrier or excipient.

Pharmaceutically acceptable carriers are generally added that are compatible with the active ingredients and acceptable for pharmaceutical use. Combinations of carriers may also be used. One of ordinary skill in the art would be familiar with pharmaceutically acceptable carriers and it is described, by way of example, in Remington's Pharmaceutical Sciences, 18th Edition, Mack Publishing Company, Pennsylvania, USA. Except insofar as any conventional media or agent is incompatible with the active ingredient, use thereof in the pharmaceutical compositions of the present invention is contemplated.

Pharmaceutical compositions for use according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound. For buccal administration the compositions may take the form of tablets or lozenges formulated in conventional manner.

The modafinil thus produced may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilizing, preserving and/or dispersing agents. Alternatively, the active ingredient may be in powder form for constitution with a suitable vehicle, e.g. sterile pyrogen-free water, before use.

In addition to the formulations described above, the modafinil in its various forms produced by the present methods may also be formulated as a depot preparation. Such long acting formulations may be administered by implantation or by intramuscular injection.

For nasal administration or administration by inhalation, the modafinil as described for use according to the present invention are conveniently delivered in the form of an aerosol spray presentation for pressurized packs or a nebulae, with the use of suitable propellant, e.g. dichlorodifluoromethane, trichloro-fluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

In another embodiment, the present invention provides methods for the treatment of a disease or disorder in a subject, comprising administering a therapeutically effective amount of a racemic mixture of modafinil obtained by subjecting benzhydrylsulfanyl carboxylic acid to an oxidation-amidation reaction using at least one microorganism to obtain a sulfoxide-amide product to a subject in need thereof. In one aspect, the sulfoxide-amide product is a racemic mixture of modafinil. As used herein, "therapeutically effective amount" refers to an amount which is effective in reducing, eliminating, treating, preventing or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

In another embodiment, a method of treating a disease or disorder in a subject, comprises administering a therapeutically effective amount of the (+)-(S)-modafinil obtained by subjecting benzhydrylsulfanyl carboxylic acid to an oxidation reaction using a microorganism to obtain an (S)-sulfoxide product; and subjecting the (S)-sulfoxide product to an amidation reaction using a microorganism to obtain an (S)-sulfoxide-amide product to a subject in need thereof. In one aspect, the sulfoxide-amide product is the (+)-(S)-enantiomer of modafinil.

In one embodiment, a method of treating a disease or disorder in a subject, comprises administering a therapeutically effective amount of (−)-(R)-modafinil obtained by subjecting benzhydrylsulfanyl carboxylic acid to an oxidation reaction using a microorganism to obtain an (R)-sulfoxide product; and subjecting the (R)-sulfoxide product to an amidation reaction using a microorganism to obtain an (R)-sulfoxide-amide product to a subject in need thereof. In one aspect, the (R)-sulfoxide-amide product is the (−)-(R)-enantiomer of modafinil.

The above pharmaceutical compositions and methods may be used to treat numerous diseases and disorders. For example, modafinil is a novel psychostimulant known to be useful in the treatment of drug addiction, for example, cocaine and amphetamine addictions, such as methamphetamine, excessive daytime sleepiness associated with narcolepsy as well as attention deficit hyperactivity disorder (ADHD), depression, hypersomnia and narcolepsy, alcoholic organic brain syndrome (OBS), obstructive sleep apnea-hypopnea syndrome (OSAHS), sleepiness, tiredness, fatigue, Alzheimer's disease, Parkinson's disease, cerebral ischemia, stroke, sleep apneas, eating disorders, urinary incontinence, ischemia, cognitive dysfunction or fatigue and for the promotion of wakefulness, stimulation of appetite, or stimulation of weight gain. Drug addiction, includes but is not limited to, the treatment of opiates, such as heroin, opium, and morphine; sympathomimetics, including cocaine and amphetamines and other drugs that mimic the stimulation of the sympathetic nervous system and for disorders of the sympathetic nervous system, for example, hypertension. The activity, methods for testing activities, dosages, dosage forms, methods of administration and background information concerning modafinil are known to one skilled in the relevant art. See, for example, Black et al., Medications for the Treatment of Narcolepsy. Expert Opin Emerg Drugs. (2001) Oct;6(2):239-47; Bastuji et al., Prog. Neuro-Psych. Biol. Psych. 12:695 (1988); U.S. Pat. No. 5,180,745; U.S. Pat. No. 4,927,855; European Published Application 547952 (published Jun. 23, 1993); and European Published Application 594507 (published Apr. 27, 1994).

As discussed above, any suitable microorganism, or suitable recombinant or mutant thereof, may be used in the processes of the present invention. As would be understood by those skilled in the art in light of the present disclosure, the conditions of the subject processes would be chosen depending upon, e.g., the kind of microorganism and the particular preparation thereof. For example, the pH, temperature, component concentrations, and the like, of the, e.g., fermentation medium and organic solvent, as well as the concentrations of the substrate and the inducer (where employed) will be chosen to provide the particular desired result using the selected microorganism.

As described earlier, any suitable preparation of the microorganism may be used in the processes of the present invention such as, for example, microorganism in growth medium, microorganism washed free of, e.g., fermentation medium, culture broth, and the like, or microorganism immobilized, e.g., in a column, attached to beads, and the like.

Those skilled in the art will understand from the description provided herein how to prepare suitable immobilized intact microorganism such as described, for example, by A. Bauer et al. in the article "Polyvinyl alcohol-immobilized whole-cell preparations for biotransformation of nitriles" published in Biotechnology Letters, 18(3): 343-348 (1996).

The microorganisms suitable for use in the oxidation and/or amidation reaction may be prepared by any suitable method known to those skilled in the relevant art. Based upon the present disclosure including the methods provided below, those skilled in the art would understand how to modify any part of these methods, e.g., method of preparing the microorganism, free or immobilized; method of contacting of the substrate with the microorganism; growth medium components and conditions, e.g., temperature, pH and the like; respective concentrations of substrate, inducer (where used); or incubation conditions; to achieve the desired result using any suitable microorganism.

The detailed examples provided below show that a range of microorganisms, in particular, fungi and bacteria, oxidize benzhydrylsulfanyl carboxylic acid to yield the corresponding sulfoxide products benzhydrylsulfinyl carboxylic acid, or (S)- or (R)-benzhydrylsulfinyl carboxylic acid, which may then be separated from any unwanted unaltered substrate, or any intermediate compounds, and further subjected to an amidation reaction with the same or another microorganism to yield a racemic mixture of modafinil, an (+)-(S)-enantiomer of modafinil or an (−)-(R)-enantiomer of modafinil. The thus produced modafinil products are useful in the treatment of a variety of diseases or conditions.

Although the present disclosure is primarily directed to the use of intact (whole) microorganisms, recombinant or mutant microorganisms, in the subject processes, those skilled in the art would understand that the processes of the present invention may be accomplished by suitable preparations thereof, e.g., broken and dehydrated cell preparations, extracted materials comprising the microbial enzymes capable of accomplishing the oxidation, amidation or oxidation-amidation reactions, or the enzymes themselves, together with any necessary cofactors, and the like.

The present invention is illustrated by the following examples. The foregoing and following description of the present invention and the various embodiments are not intended to be limiting of the invention but rather are illustrative thereof. Hence, it will be understood that the invention is not limited to the specific details of these examples.

EXAMPLES

Example 1

Introduction

Modafinil is a psychostimulant agent that has gained a lot of attention because of its recent approval by FDA for the treatment of excessive daytime sleepiness and because of its lack of abuse liability. (Zhao, S. H.; Samuel, O.; Kagan, H. B. *Tetrahedron* 1987, 43, 5135-5144; Myrick, H.; Malcolm, R.; Taylor, B.; LaRowe, S. *Ann. Clinic. Psychiatry* 2004, 16, 101-119). Recent work suggests that modafinil might also be of utility as a treatment of attention deficit/hyperactivity disorder (ADHD), and in treating opioid-induced sedation. ((a) Webster, L; Andrews, M.; Stoddard, G. *Pain Med.* 2003, 4(2), 135-40. (b) Turner D. C.; Clark, L.; Dowson, J.; Robbins, T. W.; Sahakian, B. J. *Biol. Psychiatry* 2004, 55(10), 1031-40). Although modafinil has a chiral center at the sulfur atom, the racemic sulfoxide is marketed as Provigil modafinil. (world wide web at provigil.com). The exact mechanism of action of modafinil is still unknown. Efforts are directed towards finding their mechanism of action and the physiological differences of its enantiomers.

Several methods have been devised to separate the two enantiomers of modafinil. Cephalon is currently applying a chiral stationary phase chromatography technique to separate the enantiomers in large scale. (Divide and Conquer. *Chem. Eng. News* 2004, 82(41), 20). The separation of diastereomeric salts of modafinil acid and the determination of the absolute stereochemistry of (+)- and (−)-modafinil were initially reported by Prisinzano. Prisinzano, T.; Podobinski, J.; Tidgewell, K.; Luo, M.; Swenson, D. *Tetrahedron: Asymmetry* 2004, 15, 1053-1058). The crystal structures of both enantiomers of modafinil have also been reported. (In, Y.; Tomoo, K.; Ishida, T.; Sakamoto, Y. *Chem. Pharm. Bull.* 2004, 52, 1186-1189). We reported a practical method for the preparation of both enantiomers of modafinil and its analog adrafinil, and proved unequivocally their absolute configuration, via the preparation of a diastereomeric mixture of chiral thiazolidinethione derivatives. (Osorio-Lozada, A.; Prisinzano, T.; Olivo, H. F. *Tetrahedron: Asymmetry* 2004, 15, 3811-3815).

The asymmetric syntheses of dextro and levo-modafinil should be of great interest because of the importance of studying the biological activity of each enantiomer. (Donovan, J. L.; Malcolm, R. J.; Markowitz, J. S.; DeVane, C. L. *Ther. Drug Monit.* 2003, 25(2), 197-202). Several chemical methods for the enantioselective preparation of sulfoxides are available. (Fernández, I.; Khiar, N. *Chem. Rev.* 2003, 103, 3651-3705). Chiral sulfoxides can be prepared by addition of Grignard reagents to chiral sulfinyl menthyl esters, (Andersen, K. K. *Tetrahedron Lett.* 1962, 18, 93-95) by oxidation with Kagan's (Zhao, S. H.; Samuel, O.; Kagan, H. B. *Tetrahedron* 1987, 43, 5135-5144) and Modena's (Di Furia, F.; Modena, G.; Seraglia, R. *Synthesis.* 1984, 325-326) chiral complexes, and Davis' chiral oxaziridines, (Davis, F. A.; Reddy, R. T.; Han, W.; Carroll, P. J. *J. Am. Chem. Soc.* 1992, 114, 1428-1437) among others. ((a) Evans, D. A.; Faul, M. M.; Colombo, L.; Bisaha, J. J.; Clardy, J.; Cherry, D. *J. Am. Chem. Soc.* 1992, 114, 5977-5985. (b) Tang, J.; Brackenridge, I.; Roberts, S. M.; Beecher, J.; Willets, A. J. *Tetrahedron.* 1995, 51, 13217-13238). Enantioselective sulfoxidation can also be carried out utilizing enzymatic and microbial methods. (Holland, H. L. *Chem. Rev.* 1988, 88, 473-485). Isolated enzymes such as pig liver FAD-dependent monooxygenases (Light, D. R.; Waxman, D. J.; Walsh, C. T. *Biochem.* 1982, 21, 2490-2498), chloroperoxidases from *Caldariomyces fumago* (Pasta, P.; Carrea, G.; Monzani, E.; Gaggero, N. *Biotechnol. Bioeng.* 1999, 62, 489-493), dioxygenases from *Pseudomonas* sp (Lee, K.; Brand, J. M.; Gibson, D. T. *Biochem. Biophys. Res. Comm.* 1995, 212, 9-15; Boyd, D. R.; Sharma, N. D.; Haughey, S. A.; Kennedy, M. A.; McMurray, B. T.; Sheldrake, G. N.; Allen, C. C. R.; Dalton, H.; Sproule, K. *J. Chem. Soc., Perkin Trans.* 1, 1998, 1929-1934), cyclohexanone monooxygenase from *Acinetobacter calcoaceticus* (Beard, T; Cohen, M. A.; Parratt, J. S.; Turner, N. J.; Crosby, J.; Moillet, J. *Tetrahedron: Asymmetry* 1993, 4, 1085-1104), and non-redox proteins (Dzyuba, S. V.; Klibanov, A. M. *Tetrahedron: Asymmetry* 2004, 15, 2771-2777) have been used in the syntheses of chiral sulfoxides. Whole-cell oxidations are generally preferred over the enzymatic oxidations to allow the intracellular recycle of NAD(P)H necessary in the biotransformation. (Chen, G.; Kayser, M. M.; Mihovilovic, M. D.; Mrstik, M. E.; Martinez, C. A.; Stewart, J. D. *New J. Chem.* 1999, 23, 827-832). One of the problems frequently encountered in the use of microorganisms is the number of side reactions that might occur because of the presence of several enzymes.

However, sometimes several transformations on a substrate might be desirable. In this paper, we present the synthesis of racemic and enantiomerically enriched (+)-modafinil, via a new microbial oxidation-amidation transformation.

Several wild-type and genetically modified microorganisms containing oxidative enzymes are capable to oxidize sulfides to chiral sulfoxides with high enantioselectivity. (Chen, G.; Kayser, M. M.; Mihovilovic, M. D.; Mrstik, M. E.; Martinez, C. A.; Stewart, J. D. *New J. Chem.* 1999, 23, 827-832). Although better enantioselectivities have been achieved with isolated enzymes, the use of whole cell microorganisms is more practical in the preparative production of metabolites. Interestingly, some sulfur containing compounds can be oxidized to opposite enantiomeric sulfoxides by selecting the appropriate enzyme or microorganism. (Lee, K.; Brand, J. M.; Gibson, D. T. *Biochem. Biophys. Res. Commun.* 1995, 212, 9-15; Boyd, D. R.; Sharma, N. D.; Haughey, S. A.; Kennedy, M. A.; McMurray, B. T.; Sheldrake, G. N.; Allen, C. C. R.; Dalton, H.; Sproule, K. *J. Chem. Soc., Perkin Trans.* 1, 1998, 1929-1934). Herein, we report the first enantioselective synthesis of (+)-modafinil.

Example 2

Results and Discussion

We selected benzhydrylsulfanyl acetic acid (1), easily prepared in one step (Prisinzano, T.; Podobinski, J.; Tidgewell, K.; Luo, M.; Swenson, D. *Tetrahedron: Asymmetry* 2004, 15, 1053-1058), as our initial substrate for screening several microorganisms known to possess enzymes capable of oxidizing the sulfanyl group. ((a) Holland, H. L.; Brown, F. M.; Larsen, B. G. *Bioorg. Med. Chem.* 1994, 2, 647-652. (b) Yoshida, T.; Kito, M.; Tsujii, M.; Nagasawa, T. *Biotechnol. Lett.* 2001, 23, 1217-1222. (c) Abushanab, E.; Reed, D.; Suzuki, F.; Sih, C. J. *Tetrahedron Lett.* 1978, 37, 3415-3418). A popular microorganism among synthetic chemists is the fungus *B. bassiana*. (Grogan, G. J.; Holland, H. L. *J. of Mol. Cat. B: Enzymatic.* 2000, 9, 1-32). This fungus is known to possess oxidative enzymes to hydroxylate unactivated carbons (Lehman, L. R.; Stewart, J. D. *Curr. Org Chem.* 2001, 5, 439-470) and also oxidize sulfanyl compounds. ((a) Holland, H. L.; Andreana, P. R.; Brown, F. M. *Tetrahedron: Asymmetry* 1999, 10, 2833-2843. (b) Holland, H. L.; Brown, f. *Tetrahedron: Asymmetry* 1998, 9, 535-538). We were surprisingly delighted to observe that *B. bassiana* oxidized sulfanyl 1 not only in very good yield but also with spectacular enantioselectivity furnishing the enantiomer (S)-2 (Table 1). *B. bassiana* has been used successfully in several biotransformations, but usually not very good enantioselectivity had been observed previously with this microorganism. Other fungi employed (entries 2-8) gave poor enantioselectivity, but one of them, *Microsporum gypseum*, gave the sulfinyl product in better yield (entry 3). We also found that some bacteria could give the sulfinyl product, but in low yield and low enantioselectivity (entries 9-12). We then turned our attention to recombinant *E. coli*, expressing naphthalene dioxygenase (NDO) and toluene dioxygenase (TDO) from *Pseudomonas* sp. NCIB 9816-4 and *Pseudomonas putida* F1, respectively. These two dioxygenases have been shown to oxidize sulfides to enantio-complementary sulfoxides. (Lee, K.; Brand, J. M.; Gibson, D. T. *Biochem. Biophys. Res. Commun.* 1995, 212, 9-15; Boyd, D. R.; Sharma, N. D.; Haughey, S. A.; Kennedy, M. A.; McMurray, B. T.; Sheldrake, G. N.; Allen, C. C. R.; Dalton, H.; Sproule, K. *J. Chem. Soc., Perkin Trans.* 1, 1998, 1929-1934). Indeed, these recombinant strains gave the expected opposite sulfinyl products, but in poor yields and also poor enantioselectivities. The recombinant *E. coli* CPMO and CHMO, overexpressing cyclopentanone monooxygenase from *Pseudomonas* sp. NCIMB 9872 and cyclohexanone monooxygenase from *Acinetobacter* sp. NCIMB 9871, respectively, also gave the sulfinyl product in 16% and 73% yields with poor enantioselectivity, but complementary stereochemistry.

TABLE 1

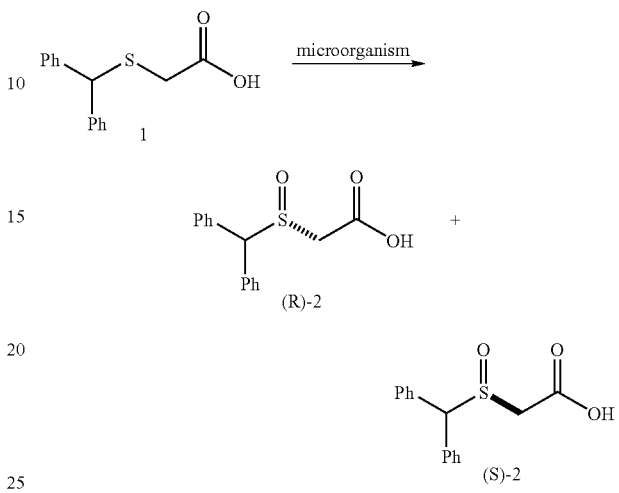

Microbial sulfoxidation of benzhydrylsulfanyl acetic acid.

| Entry | Microorganism | Major isomer | ee (%) | Yield (%) |
|---|---|---|---|---|
| 1 | *Beauveria bassiana* (ATCC-7159) | S | 99 | 89 |
| 2 | *Mortierella isabellina* (ATCC-38063) | S | 33 | 66 |
| 3 | *Microsporum gypseum* (ATCC-11395) | S | 1 | 94 |
| 4 | *Thamnidium elegans* (ATCC-18191) | S | 3 | 77 |
| 5 | *Caldariomycesfumago* (ATCC-16373) | S | 9 | 18 |
| 6 | *Cylindrocarpon radicicola* (ATCC-11011) | R | 5 | 6 |
| 7 | *Cunninghamella echinulata* (ATCC-9244) | S | 16 | 38 |
| 8 | *Mortierella elongata* (NRRL-5513) | S | 3 | 19 |
| 9 | *Sphingomonas* sp. HXN-200 | R | 40 | 32 |
| 10 | *Rhodococcus rhodochrous* (ATCC-21 197) | R | 0.6 | 17 |
| 11 | *Helminthosporium* sp. (NRRL-4671) | S | 3 | 36 |
| 12 | *Bacillus subtilis* IFO-3108 | — | — | 2 |
| 13 | *E. coli* NIDO (pDTG141) | S | 36 | 16 |
| 14 | *E. coli* TDO (pDTG601A) | R | 37 | 40 |
| 15 | *E.coli* CPMO | S | 36 | 16 |
| 16 | *E.coli* CHMO | R | 21 | 73 |

In efforts to find microorganisms that could oxidize the sulfanyl group to the complementary enantiomeric sulfoxide of the one obtained with *B. bassiana*, another substrate, benzhydrylsulfanyl acetamide (3), was then investigated (Table 2). Compound 3 was prepared from benzhydrylsulfanyl acetic acid via acid chloride formation followed by addition to a solution of ammonium hydroxide in THF in 96% yield. Compound 3 was also directly prepared from benzhydrylsulfanyl acetic acid and urea-imidazole under microwave irradiation (Khalafi-Nezhad, A.; Mokhtari, B.; Soltani Rad, M. N. *Tetrahedron Lett.* 2003, 44, 7325-7328) in 85% yield and also by lipase-mediated ammoniolysis in 91% yeild when Novozyme-435 was used. ((a) Litjens, M. J. J.; Straathof, A. J. J.; Jongejan, J. A.; Heijnen, J. J. *Chem. Commun.* 1999, 1255-1256. (b) Lau, R. M.; van Rantwijk, F.; Seddon, K. R.; Sheldon, R. A. *Org. Lett.* 2000, 2, 4189-4191). Interestingly, biotransformation of 3 with *B. bassiana* afforded the (R)- isomer of modafinil in good yield, but low ee. Other microorganisms provided the oxidized (S)-isomer also with low yields and enantioselectivities. *Microsporum gypseum* and *Thamnidium elegans* oxidized both the sulfanyl acid 1 and also sulfanyl amide 3 (entries 2 and 3). When sulfanyl acetamide 3 was biotransformed with *Amycolatopsis orientalis*, modafinil was obtained in very good yield but almost no enantioselectivity (entry 4).

TABLE 2

Microbial sulfoxidation of benzhydrylsulfanyl acetamide.

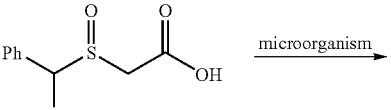

| Entry | Microorganism | Major isomer | % ee | yield |
|---|---|---|---|---|
| 1 | *Beauveria bassiana* (ATCC-7159) | R | 22 | 67 |
| 2 | *Microsporum gypseum* (ATCC-11395) | S | 49 | 37 |
| 3 | *Thamnidium elegans* (ATCC-18191) | S | 15 | 42 |
| 4 | *Amycolotopsis orientalis* (ATCC-19795) | S | 5 | 91 |
| 5 | *E. coli* CPMO | S | 47 | 6 |
| 6 | *E. coli* CHMO | R | 25 | 31 |
| 7 | *E. coli* NDO (pDTG141) | — | — | 2 |
| 8 | *E. coli* TDO (pDTG601A) | — | — | 2 |

Strikingly, when benzhydrylsulfanyl acetic acid (1) was fermented with the fungus *Amycolatopsis orientalis*, both amidation of the carboxylic acid and oxidation of the sulfanyl to the sulfoxide group took place, albeit with no enantioselectivity, furnishing racemic modafinil (Scheme 1). Interestingly, only a few isolated cases of direct amidation of carboxylic acids employing microorganisms can be found in the literature. ((a) Brunati, M.; Marinelli, F.; Bertolini, C.; Gandolfi, R.; Daffonchio, D.; Molinari, F. *Enzyme Microb. Technol.* 2004, 34, 3-9. (b) Maruyama, R.; Ono, S.; Inoue, M. *Tetrahedron Lett.* 2000, 41, 5229-5232). A lot of work has been devoted to the enzymatic hydrolysis of nitriles to furnish amides with high enantioselectivity. (Beard, T.; Cohen, M. A.; Parratt, J. S.; Turner, N. J.; Crosby, J.; Moillet, J. *Tetrahedron. Asymmetry* 1993, 4, 1085-1104).

Scheme 1. Biotransformation of 1 with A. orientalis.

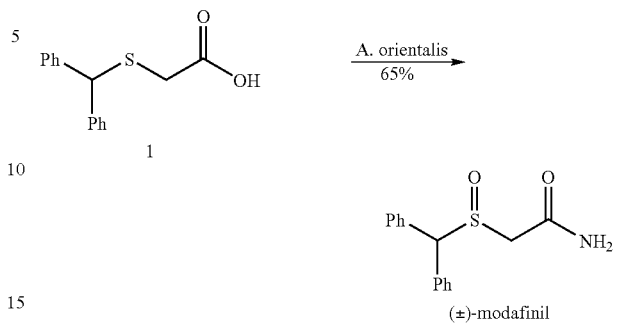

These results directed us to study the biotransformation of racemic and enantiomerically pure β-sulfinyl carboxylic acids 2 with *A. orientalis* (Table 3). It's noteworthy to say that lipase-mediated ammoniolysis ((a) Litjens, M. J. J.; Straathof, A. J. J.; Jongejan, J. A.; Heijnen, J. J. *Chem. Commun.* 1999, 1255-1256. (b) Lau, R. M.; van Rantwijk, F.; Seddon, K. R.; Sheldon, R. A. *Org Lett.* 2000, 2, 4189-4191) and microwave accelerated amidation (Khalafi-Nezhad, A.; Mokhtari, B.; Soltani Rad, M. N. *Tetrahedron Lett.* 2003, 44, 7325-7328) reactions were not successful with compound 2. When racemic-2 was used as substrate with *A. orientalis*, the (S)-modafinil was obtained in low yield and low enantioselectivity (entry 1). When enantiopure (R)-2 and (S)-2 were used as substrates, prepared by hydrolysis of chiral thiazolidinethione diastereomers, (Osorio-Lozada, A.; Prisinzano, T.; Olivo, H. F. *Tetrahedron: Asymmetry* 2004, 15, 3811-3815) (R)- and (S)-modafinil were obtained in low yields without racemization (entries 2 and 3). Several *Bacillus* species were also screened for the amidation of sulfinyl carboxylic acid 2. Better yield was obtained for the amidation of racemic-2 with *B. subtilis* var. *niger*, but no selectivity was observed (entries 2 and 3). Also, better yields were obtained in the amidation of enantiopure 2 with *B. subtilis* (entries 4-6).

TABLE 3

Microbial amidation of benzhydrylsulfinyl acetic acid.

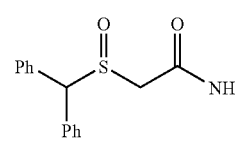

| Entry | Microorganism | 2 | Modafinil (%) | ee (%) |
|---|---|---|---|---|
| 1 | *Amycolatopsis orientalis* (ATCC-19795) | R,S | 43 (S) | 38 |
| 2 | *Amycolatopsis orientalis* (ATCC-19795) | R | 100 (R) | 22 |
| 3 | *Amycolatopsis orientalis* (ATCC-19795) | S | 100 (S) | 28 |
| 4 | *Bacillus subtilis* var. niger (IFO-3180) | R,S | — | 81 |

TABLE 3-continued

Microbial amidation of benzhydrylsulfinyl acetic acid.

$$\text{Ph}\diagdown\text{CH}(\text{Ph})\text{-S}(\text{O})\text{-CH}_2\text{-C}(\text{O})\text{OH} \quad \xrightarrow{\text{microorganism}}$$

2

$$\text{Ph}\diagdown\text{CH}(\text{Ph})\text{-S}(\text{O})\text{-CH}_2\text{-C}(\text{O})\text{NH}_2$$

modafinil

| Entry | Microorganism | 2 | Modafinil (%) | ee (%) |
|---|---|---|---|---|
| 5 | *Bacillus subtilis* var. niger (IFO-3180) | R | 100 (R) | 60 |
| 6 | *Bacillus sublilis* var. niger (IFO-3180) | S | 100 (S) | 68 |

Example 3

Conclusion

To our knowledge, this is the first report of a biocatalytic one-flask oxidation/amidation utilizing a whole-cell transformation. The synthesis of racemic modafinil described here, was accomplished utilizing two strategies: (a) one chemical and one-flask-two-microbial transformations (65% overall yield) and (b) one chemical, one chemo-enzymatic and one microbial transformations (81% overall yield). The enantioselective synthesis of (S)-modafinil was accomplished in three steps, one chemical step and two microbial transformations (60% overall yield). These syntheses of modafinil are extremely short and represent low environmental impact chemical processes.

Example 4

General Information

The microorganisms used were obtained from the American Type Culture Collection (ATCC), except for the strains obtained from the research groups cited in the Acknowledgments section. Enantiomeric excesses were determined by chiral HPLC using a Cyclobond I-200 RSP column (250×4.6 mm).

Example 5

Benzhydrylsulfanyl acetic acid (1)

This compound was prepared according to the procedure of Prisinzano. (Prisinzano, T.; Podobinski, J.; Tidgewell, K.; Luo, M.; Swenson, D. *Tetrahedron: Asymmetry* 2004, 15, 1053-1058). The synthesis employed benzhydrol (50.0 g, 271.4 mmol) and thioglycolic acid (25.0 g, 271.4 mmol) to give the title compound as a white solid: 69.2 g (99% yield); mp 126-129° C. Spectroscopic data was identical to lit. (Prisinzano, T.; Podobinski, J.; Tidgewell, K.; Luo, M.; Swenson, D. *Tetrahedron: Asymmetry* 2004, 15, 1053-1058).

Example 6

2-Benzhydrylsulfanyl acetamide (3)

Chemical method: This compound was obtained from the corresponding acid chloride. To a solution of acid 1 (777 mg, 3 mmol) in benzene was added $SOCl_2$ (833 mg, 7 mmol). The solution was heated to reflux for 1 hour. The solvent was evaporated to give a yellow oil: 832.1 mg (99.9%). A solution of benzhydrylsulfanyl acetyl chloride (1.089 g, 4.21 mmol) in $CH_2Cl_2$ (10 mL) was added to a solution of $NH_4OH$-THF (3:2, 30 mL) at 0° C. The reaction was stirred for 1 hour. The reaction mixture was then treated with $H_2O$ (20 mL) and extracted with $CH_2Cl_2$ (2×30 mL). The organic layer was washed with saturated $NaHCO_3$ (20 mL) and $H_2O$ (20 mL). The organic layer was dried over $Na_2SO_4$, filtered and concentrated under reduced pressure. The residue was purified by flash column chromatography on a silica gel column (3×10 cm). Elution with 9:1 $CHCl_3$-MeOH gave a light yellow solid: 1.044 g (96%).

Chemo-enzymatic method: To a solution of Benzhydrylsulfanyl acetic acid (259 mg, 1.0 mmol) in tert-butanol (28 mL) was added ammonium carbamate (79 mg, 1.0 mmol) and Novozyme-435 (100 mg). The reaction flask was closed tightly and the reaction was stirred at 60° C. for 7 days. The reaction mixture was filtered through cotton plug and concentrated under vacuum to give a colourless turbid oil. The crude oil was purified by flash column chromatography on silicagel (2×9 cm). Elution with hexanes-ethyl acetate (3:2) furnished the sulfanyl amide as a light yellow solid: 232 mg (90% yield). Silica gel TLC $R_f$ 0.26 (1:1 hexanes:ethyl acetate); Silica gel TLC $R_f$ 0.60 (9:1 chloroform-methanol); mp 109-110° C.; $^1$H NMR ($CDCl_3$) δ 7.43-7.31 (10H, m), 6.52 (1H, bs), 5.87 (1H, bs) 5.17 (1H, s), 3.08 (2H, s); $^{13}$C NMR ($CDCl_3$) δ 171.5 (CO), 140.4 (2C), 128.9 (4CH), 128.4 (4CH), 127.8 (2CH), 54.9 (CH), 35.7 ($CH_2$).

Example 7

4.4 (+)-(S)-(Diphenylmethanesulfinyl)acetic acid (+)-2

A culture of *Beauveria bassiana* (ATCC-7159) was obtained from ATCC and transferred onto potato dextrose agar slants using techniques described by ATCC and those provided with the culture. The culture was grown at 28° C. for 7 days, sealed and stored at 4° C. Subculturing was performed every two weeks, with cultures ready for use after 5 days of growth at 28° C. Stage I cultures were grown from potato dextrose agar slants in 25 mL of Iowa medium in 125 mL DeLong flask. Flasks were shaken at 250 rpm and 28° C. for 72 hours. Stage II cultures were grown from Stage I cultures in 200 mL of Iowa medium in 1 L DeLong flasks. After 24 hours of growth, substrate (200 mg, 0.77 mmol) was added as a solution in dimethylformamide (1 mL). The reaction was monitored by thin-layer chromatography by taking samples at 24, 48, 72, and 144 hours. After 5-7 days the fermentation broth was filtered through cheesecloth. The filtrate was loaded into a glass column containing a Dowex 1X2-200 ion-exchange resin (previously washed with 0.5 N NaOH solution (50 mL) and deionized water (100 mL)). The crude sulfinyl-acid was eluted with 0.5 N HCl solution. The fractions containing the sulfinyl-acid were extracted with ethyl acetate (2×50 mL). The combined organic layers were dried over anhydrous sodium sulfate, filtered and concentrated to give the title product as a white solid: 189 mg (89%). Silica gel TLC $R_f$ 0.36 (7:3 chloroform-methanol); mp 118-120° C.; $[\alpha]_D^{22}$=+38.3 (c 1.0, $CH_3OH$); ee 99.1%, Chiral HPLC analysis. Column: Cyclobond I-200 RSP: UV detector: λ 225 nm; solvent: 0.02 M phosphate buffer (pH 3)-acetonitrile, 85:15; flow rate: 0.6 mL/min; retention time: (+)-2, 34.8 min; (−)-2, 36.8 min.

IR υ 2925, 2778, 2527, 1716, 1500, 1451, 1287, 1187, 1016, 750, 704 $cm^{-1}$; $^1H$ NMR ($CDCl_3$) δ 7.56-7.51 (4H, m), 7.44-7.32 (6H, m), 5.40 (1H, s), 3.41 (1H, d, J=13.7 Hz), 3.23 (1H, d, J=13.7 Hz); $^1H$ NMR (acetone-$d_6$) δ 7.63-7.57 (4H, m), 7.47-7.33 (6H, m), 5.35 (1H, s), 3.62 (1H, d, J=14.2 Hz), 3.41 (1H, d, J=14.2 Hz); $^{13}C$ NMR ($CDCl_3$) δ 166.6 (CO), 134.4 (C), 133.9 (C), 129.8 (2CH), 129.6 (2CH), 129.2 (2CH and CH), 129.0 (CH), 128.9 (2CH), 71.5 (CH), 50.9 ($CH_2$). $^{13}C$ NMR (acetone-$d_6$) δ 167.3 (CO), 137.6 (C), 135.8 (C), 129.8 (2CH), 129.1 (2CH), 128.7 (2CH), 128.5 (2CH), 128.2 (CH), 128.1 (CH), 71.4 (CH), 55.4 ($CH_2$).

Example 8

(+)-(S)-(Diphenylmethanesulfinyl)acetamide (+)-modafinil

Stage I cultures of *Bacillus subtilis* were grown from nutrient agar slants in 25 mL of Iowa medium in 125 mL DeLong flask. Flasks were shaken at 250 rpm and 28° C. for 72 hours. Stage II cultures were grown from stage I cultures in 200 mL of Iowa medium in 1 L DeLong flasks. After 24 hours of growth, (+)-(diphenylmethanesulfinyl)acetic acid (200 mg, 0.77 mmol, ee 100%) was added as a solution in dimethylformamide (1 mL). The reaction was monitored by thin layer chromatography by taking samples at 24, 48, 72 and 144 hours. After 7 days the cells were separated by centrifugation at 4° C. The decanted fermented broth was extracted with chloroform in a liquid-liquid continuous extractor. The organic layer was concentrated under vacuum to give a light yellow oil. The oil residue was purified by flash column chromatography on a silica gel (2 cm×10 cm). Elution with gradient 1-5% MeOH—$CHCl_3$ afforded the modafinil as white solid 135 mg (68%). Silica gel TLC $R_f$ 0.48 (9:1 chloroform-methanol); mp 158-159° C.; $[\alpha]_D^{22}$=+79 (c 1.0, $CHCl_3$); ee 100%, Chiral HPLC analysis. Column: Cyclobond I-200 RSP: UV detector: λ 225 nm; solvent: 0.02 M phosphate buffer (pH 3)-acetonitrile, 85:15; flow rate: 0.6 mL/min; retention time: (+)-1, 23.0 min; (−)-1, 25.1 min. IR υ 3383, 3314, 3257, 3191, 1690, 1617, 1495, 1376, 1027, 702 $cm^{-1}$. $^1H$ NMR ($CDCl_3$) δ 7.51-7.48 (2H, m), 7.45-7.32 (8H, m), 7.07 (1H, bs), 5.88 (1H, d, bs), 5.24 (1H, s), 3.47 (1H, d, J=14.2 Hz), 3.14 (1H, d, J=14.2 Hz); $^{13}C$ NMR ($CDCl_3$) δ 166.5 (C), 134.7 (C), 134.3 (C), 129.62 (2CH), 129.58 (2CH), 129.1 (2CH), 128.98 (3CH), 128.8 (CH), 71.6 (CH), 52.0 ($CH_2$);

What is claimed is:

1. A method of preparing an (S)-enantiomer of modafinil (2-[(diphenylmethyl)sulfinyl]acetamide) comprising:
    (a) subjecting benzhydrylsulfanyl carboxylic acid to an oxidation reaction using a microorganism to obtain an (S)-sulfoxide product of (S)-benzhydrylsulfinyl carboxylic acid; and
    (b) subjecting the (S)-sulfoxide product to an amidation reaction using a microorganism to obtain an (S)-sulfoxide-amide product of (+)-(S)-modafinil.

2. The method of claim 1 wherein the same microorganism is used in the oxidation and amidation reactions.

3. The method of claim 1 wherein the microorganism used for the oxidation reaction is a bacteria, yeast, or fungus.

4. The method of claim 1 wherein the microorganism used for the amidation reaction is a bacteria, yeast, or fungus.

5. The method of claim 3 wherein the bacteria used for the oxidation reaction is genetically engineered to express at least one oxygenase.

6. The method of claim 5 wherein the oxygenase is selected from the group consisting of dioxygenase, napthalene dioxygenase, toluene dioxygenase, chloroperoxidase, monooxygenase, cyclopentanone monooxygenase, cyclohexanone monooxygenase.

7. The method of claim 3 wherein the microorganism used for the oxidation reaction is selected from the group consisting of *Beauveria bassiana, Microsporum gypseum, Mortierella isabellina, Caldariomycesfumago, Mortierella elongata, Helminthosporium* sp, *Amycolaptosis orientalis, Thamnidium elegans*.

8. The method of claim 4 wherein the bacteria used for the amidation reaction is *Bacillus subtilis* or *Amycolaptosis orientalis*.

9. A method of preparing an (+)-(S)-enantiomer of modafinil (2-[(diphenylmethyl)sulfinyl]acetamide) comprising:
    (a) subjecting benzhydrylsulfanyl carboxylic acid to an oxidation reaction using *Beauveria bassiana* to obtain (S)-benzhydiylsulfinyl carboxylic acid; and
    (b) subjecting the (S)-benzhydrylsulfinyl carboxylic acid to an amidation reaction using *Bacillus subtilis* to obtain (+)-(S)-modafinil.

10. A method of preparing (−)-(R)-enantiomer of modafinil (2-[(diphenylmethyl)sulfinyl]acetamide) comprising:
    (a) subjecting benzhydrylsulfanyl carboxylic acid to an oxidation reaction using a microorganism to obtain an (R)-sulfoxide product of (R)-benzhydrylsulfinyl carboxylic acid; and
    (b) subjecting the (R)-sulfoxide product to an amidation reaction using a microorganism to obtain an (R)-sulfoxide-amide product of (−)-(R)-modafinil.

11. The method of claim 10 wherein the same microorganism is used in the oxidation and amidation reactions.

12. The method of claim 10 wherein the microorganism used for the oxidation reaction is a bacteria, yeast, or fungus.

13. The method of claim 10 wherein the microorganism used for the amidation reaction is a bacteria, yeast, or fungus.

14. The method of claim 12 where the microorganism is selected from the group consisting of *Rhodococcus rhodochrous* or *Sphingomonas* sp. and *Cylindrocarpon radicicola*.

15. The method of claim 12 wherein the bacteria used for the oxidation reaction is genetically engineered to comprises at least one oxygenase.

16. The method of claim 15 wherein the oxygenase is a dioxygenase, napthalene dioxygenase, toluene dioxygenase, monooxygenase, alkane monooxygenase, cyclohexanone monooxygenase.

17. The method of claim 13 wherein the bacteria used for the amidation reaction is *Bacillus subtilis* or *Amycolaptosis orientalis*.

18. A method of preparing an (−)-(R)-enantiomer of modafinil (2-[(diphenylmethyl)sulfinyl]acetamide) comprising:
    (a) subjecting benzhydrylsulfanyl carboxylic acid to an oxidation reaction using *Sphingomonas* sp to obtain (R)-benzhydrylsulfinyl carboxylic acid; and
    (b) subjecting the (R)-benzhydrylsulfinyl carboxylic acid to an amidation reaction using the bacteria genetically engineered comprising toluene dioxygenase to obtain (−)-(R)-modafinil.

* * * * *

UNITED STATES PATENT AND TRADEMARK OFFICE
CERTIFICATE OF CORRECTION

| | | |
|---|---|---|
| PATENT NO. | : 7,553,646 B2 | |
| APPLICATION NO. | : 11/460532 | |
| DATED | : June 30, 2009 | |
| INVENTOR(S) | : Horacio F. Olivo et al. | |

It is certified that error appears in the above-identified patent and that said Letters Patent is hereby corrected as shown below:

Col. 1, Lines 8-11:
DELETE "This invention was partially funded by the National Science Foundation, No. EEC-0310689. The government may have certain rights in the invention."

ADD --This invention was made with government support under EEC-0310689 awarded by the National Science Foundation. The government has certain rights in the invention.--

Col. 30, Claim 6, line 11:
After monooxygenase, add --and--

Col. 30, Claim 7, Line 15:
After *isabellina*, delete "*Caldariomycesfumago*"
After *isabellina*, add --*Caldariomyces fumago*--

Col. 30, Claim 7, Line 16:
After *orientalis*, add --and--

Col. 30, Claim 9, Line 25:
After an, delete "(S)-benzhydiylsulfinyl"
After an, add --(S)-benzhydrylsulfinyl--

Col. 30, Claim 14, Line 45:
After *rhodochrous*, delete "or"
After *rhodochrous*, add --,--

Col. 30, Claim 15, Line 47:
After to, delete "comprises"
After to, add --comprise--

Col. 30, Claim 16, Line 51:
After monooxygenase, add --or--

UNITED STATES PATENT AND TRADEMARK OFFICE
CERTIFICATE OF CORRECTION

PATENT NO. : 7,553,646 B2
APPLICATION NO. : 11/460532
DATED : June 30, 2009
INVENTOR(S) : Horacio F. Olivo et al.

It is certified that error appears in the above-identified patent and that said Letters Patent is hereby corrected as shown below:

Col. 30, Claim 18, Line 63:
After engineered, delete "comprising"
After engineered, add --to comprise--

Signed and Sealed this

Twenty-second Day of September, 2009

David J. Kappos
*Director of the United States Patent and Trademark Office*